US010512687B2

(12) United States Patent
Dow et al.

(10) Patent No.: US 10,512,687 B2
(45) Date of Patent: Dec. 24, 2019

(54) COMPOSITIONS AND METHODS FOR ENHANCED INNATE IMMUNITY

(71) Applicants: Colorado State University Research Foundation, Fort Collins, CO (US); The Regents of the University of Colorado, a body corporate, Denver, CO (US)

(72) Inventors: Steven Dow, Littleton, CO (US); Michael R. Lappin, Fort Collins, CO (US); William H. Wheat, Fort Collins, CO (US); Lyndah Chow, Fort Collins, CO (US); Daniel P. Regan, Fort Collins, CO (US); Thomas J. Anchordoquy, Lakewood, CO (US)

(73) Assignees: Colorado State University Research Foundation, Fort Collins, CO (US); The Regents of the University of Colorado, a body corporate, Denver, CO (US)

( * ) Notice: Subject to any disclaimer, the term of this patent is extended or adjusted under 35 U.S.C. 154(b) by 97 days.

(21) Appl. No.: 15/476,723

(22) Filed: Mar. 31, 2017

(65) Prior Publication Data

US 2017/0281754 A1     Oct. 5, 2017

Related U.S. Application Data

(60) Provisional application No. 62/456,505, filed on Feb. 8, 2017, provisional application No. 62/316,985, filed on Apr. 1, 2016, provisional application No. 62/316,986, filed on Apr. 1, 2016.

(51) Int. Cl.

| | |
|---|---|
| *A61K 8/14* | (2006.01) |
| *A61K 39/39* | (2006.01) |
| *C12N 15/117* | (2010.01) |
| *A61K 47/69* | (2017.01) |
| *A61K 39/12* | (2006.01) |
| *A61K 49/00* | (2006.01) |
| *A61K 39/00* | (2006.01) |

(52) U.S. Cl.
CPC ............... *A61K 39/39* (2013.01); *A61K 8/14* (2013.01); *A61K 39/12* (2013.01); *A61K 47/6911* (2017.08); *C12N 15/117* (2013.01); *A61K 49/0054* (2013.01); *A61K 49/0084* (2013.01); *A61K 2039/53* (2013.01); *A61K 2039/543* (2013.01); *A61K 2039/545* (2013.01); *A61K 2039/552* (2013.01); *A61K 2039/555* (2013.01); *A61K 2039/55511* (2013.01); *A61K 2039/55516* (2013.01); *A61K 2039/55555* (2013.01); *A61K 2039/55561* (2013.01); *A61K 2039/57* (2013.01); *C12N 2710/16034* (2013.01)

(58) Field of Classification Search
CPC ...... A61K 2039/55555; A61K 2039/53; A61K 39/39; A61K 39/12; A61K 2039/543; A61K 2039/57; A61K 2039/55561; A61K 2039/545; A61K 2039/552; A61K 2039/55511; A61K 2039/55516; A61K 35/68

See application file for complete search history.

(56) References Cited

U.S. PATENT DOCUMENTS

| | | | |
|---|---|---|---|
| 6,251,678 B1 | 6/2001 | Volkin et al. | |
| 2005/0013812 A1* | 1/2005 | Dow ...................... | A61K 39/02 424/144.1 |
| 2010/0297165 A1 | 11/2010 | Berzofsky et al. | |
| 2011/0070298 A1* | 3/2011 | Mansour .................. | A61K 9/10 424/450 |

FOREIGN PATENT DOCUMENTS

| | | |
|---|---|---|
| WO | 2008057696 | 5/2008 |
| WO | 2010060030 | 5/2010 |
| WO | WO-2016161309 A1 * | 10/2016 |

OTHER PUBLICATIONS

Bal et al. Co-encapsulation of antigen and Toll-like receptor ligand in cationic liposomes affects the quality of the immune response in mice after intradermal vaccination. Vaccine 29: 1045-1052, 2011.*
Diwan et al. Enhancement of immune responses by co-delivery of a CpG oligodeoxynucleotide and tetanus toxoid in biodegradable nanospheres. J Controlled Release 85: 247-262, 2002.*
Dow et al. Liposome-nucleic acid immunotherapeutics. Expert Opin Drug Delivery 5(1): 11-24, 2008.*
Graciotti et al. The era of bioengineering: how will this affect the next generation of cancer immunotherapy? J Transl Med 15: 142, 2017.*
Kawakami et al. Effect of hydrophilic polymers on physical stability of liposome dispersions. J Phys Chem B 105: 2374-2385, 2001.*
Lee et al. Biodegradable nanoparticles containing TLR3 or TLR9 agonists together with antigen enhance MHC-restricted presentation of the antigen. Arch Pharm Res 33(11): 1859-1866, 2010.*
Milicic et al. Small cationic DDA:TDB liposomes as protein vaccine adjuvants obviate the need for TLR agonists in inducing cellular and humoral responses. PLoS One 7(3): e34255, 2012.*

(Continued)

*Primary Examiner* — Bridget E Bunner
(74) *Attorney, Agent, or Firm* — Polsinelli PC

(57) ABSTRACT

The disclosed compositions and methods relate to an immunogenic composition that, in certain aspects, comprise cationic liposomes; a mixture of toll like receptor 3 (TLR3) and toll like receptor 9 (TLR9) ligands; and a cellular adhesion agent, and methods of using such compositions. In certain aspects, disclosed compositions are administered to a mammal to induce a non-specific innate immune response at mucosal surfaces. In further aspects, disclosed compositions are administered to a mammal in conjunction with an antigen to enhance the immune response of the mammal to the antigen.

17 Claims, 34 Drawing Sheets

Specification includes a Sequence Listing.

(56) References Cited

OTHER PUBLICATIONS

Patel et al. Novel drugs targeting Toll-like receptors for antiviral therapy. Future Virol 9(9): 811-829, 2014.*
Suzuki et al. Liposome-encapsulated CpG oligonucleotides as a potent adjuvant for inducing Type 1 innate immunity. Cancer Res 64: 8754-8760, 2004.*
Temizoz et al. Vaccine adjuvants as potential cancer immunotherapeutics. Int Immunol 28(7): 329-338, 2016.*
Uematsu et al. Toll-like receptors (TLRs) and their ligands. "Toll-like receptors (TLRs) and Innate Immunity" in Handbook of Experimental Pharmacology 183: 1-20, 2008.*
Wong et al. Activation of toll-like receptor signaling pathway for protection against influenza virus infection. Vaccine 27: 3481-3483, 2009.*
Zaks et al. Efficient immunization and cross-priming by vaccine adjuvants containing TLR3 or TLR9 agonists complexed to cationic liposomes. J Immunol 176: 7335-7345, 2006.*
Gowan et al. Prophylaxis with cationic liposome-DNA complexes protects hamsters from phleboviral disease: importance of liposomal delivery and CpG motifs. Antiviral Res 81: 37-46, 2009.*
Grossman et al. Enhancement of the priming efficacy of DNA vaccines encoding dendritic cell-targeted antigens by synergistic toll-like receptor ligands. BMC Immunol 10: 43, 2009 (10 total pages).*
Henderson et al. Mucosal immunization with liposome-nucleic acid adjuvants generates effective humoral and cellular immunity. Vaccine 29: 5304-5312, 2011.*

\* cited by examiner

Greater retention of PCT-01 in nasal cavity of mice at 60 minutes compared to CLDC ("CALNAC")

Increased infiltration of immune cells taking up liposomes in nose of cats administered PCT-01 than cats treated with CLDC Oral administration of PCT-01 elicits greater infiltrate of immune cells in the oropharynx than CLDC administration (oral CLDC administration) TopFluor® + throat swab (oral PCT-01 administration) TopFluor® + throat swab Uptake of labeled PCT-01 ("MIM") by nasal lavage cells and throat cells following intranasal and oral administration in healthy dog
FIG. 13A (labeled MIM uptake by nasal lavage cells)
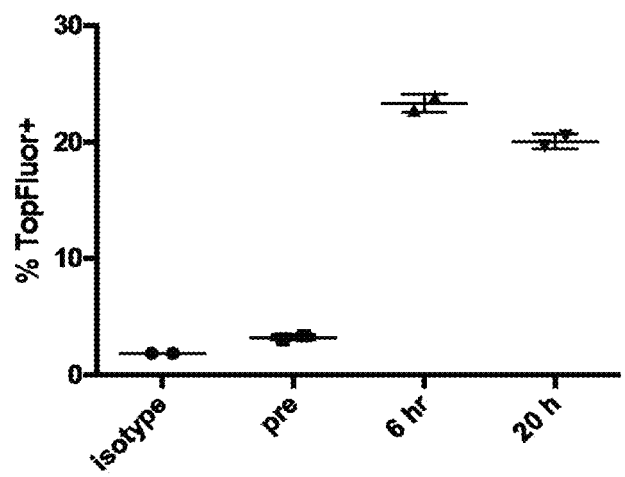
FIG. 13B (labeled MIM uptake by throat swab cells)
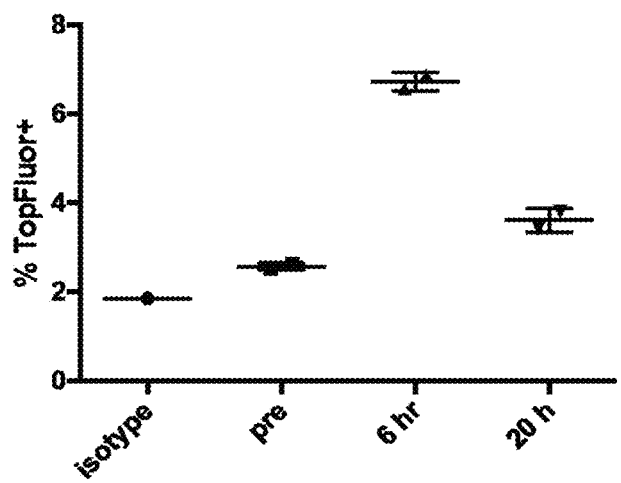

Stimulation of neutrophil infiltrates into nose and monocyte infiltrates into throat of dog treated with PCT-01

(Neutrophil infiltrate into nose)

(Monocyte infiltrate into throat)

Stimulation of CD4 T cell infiltrate into nose and throat of dog following PCT-01 treatment (CD4 T cell infiltration: nasal lavage)

(CD4 T cell infiltration: throat swabs)

Changes in nasopharyngeal cell counts over time following PCT-01 ("MIM") administration

Effects of PCT-01 ("MIM") administration on monocyte recruitment and immune activation (nasopharyngeal swab specimens)

Effect of PCT-01 ("MucosImmune") and Zelnate treatment on body temperature at 24h More potent and rapid induction of IL-8 expression by nasopharyngeal cells in cattle following administration of PCT-01 ("MIM") than after Zelnate administration More potent and rapid induction of IFN-a expression by nasopharyngeal cells in cattle following administration of PCT-01 ("MIM") than after Zelnate administration More potent and rapid induction of MCP-1 expression by nasopharyngeal cells in cattle following administration of PCT-01 ("MIM") than after Zelnate administration Cellular response to PCT-01 infusion in the mammary gland of cattle. Increased infiltration of mononuclear cells (lymphocytes, right panel) in the milk of cattle treated by intra-mammary infusion of PCT-01 24h previously. Untreated milk (left panel) contains primarily milk macrophages, with rare lymphocytes.

Immune cell recruitment and activation in goat nasopharynx following intranasal PCT-01 ("MIM") administration in goats

COMPOSITIONS AND METHODS FOR ENHANCED INNATE IMMUNITY

CROSS-REFERENCE TO RELATED APPLICATION(S)

This application claims priority to U.S. Provisional Application No. 62/316,986 filed Apr. 1, 2016 and entitled "Enhanced Liposomal Immunotherapeutic for Vaccination;" U.S. Provisional Application No. 62/316,985 filed Apr. 1, 2016 and entitled "Compositions and Methods for Stimulating Mucosal Innate Immune Response;" and U.S. Provisional Application No. 62/456,505 filed Feb. 8, 2017 and entitled "Mucosal immune stimulant for eliciting non-specific protection from viral and bacterial pathogens" each of which is hereby incorporated by reference in its entirety under 35 U.S.C. § 119(e).

TECHNICAL FIELD

The disclosure relates to novel immunostimulatory compositions, adjuvants and vaccines, and their use to stimulate immune responses and treat or prevent diseases and infections.

BACKGROUND

There is a growing need for new approaches for generating non-specific protection from viral and bacterial infections without having to resort to the use of antibiotics or other antimicrobial drugs, which serve to stimulate the development of antibiotic resistance. Currently however there are few immunostimulatory compounds that are capable of eliciting rapid and sustained activation of innate immune responses at mucosal surfaces such as the nasopharynx, upper respiratory tract, GI tract, and reproductive tract to generate protection from infection. The current invention is a composition designed to adhere to and rapidly activate immunity at mucosal surfaces, and to also persist in this location and generate sustained local immune activation. By so doing, this mucosal immune stimulatory composition generates non-specific protection from infection with pathogens including bacteria and viruses that infect the respiratory tract and other mucosal surfaces.

There is a need in the art for novel compositions and methods to enhance innate immune responses at mucosal surfaces for non-specific protection from viral or bacterial infections, as well as to increase the efficacy of existing vaccines.

BRIEF SUMMARY

Disclosed herein an immunogenic composition comprising (a) cationic liposomes, (b) a mixture of toll like receptor 3 (TLR3) and toll like receptor 9 (TLR9) ligands, and (c) a cellular adhesion agent. In certain aspects, the cationic liposomes include a mixture of cationic lipid and non-charged lipids, optionally DOTAP and cholesterol, in a 1:1 molar ratio. In further aspects, the mixture includes non-coding plasmid DNA and polyI:C. In certain further aspects, the non-coding plasmid DNA includes a polynucleotide of SEQ ID NO. 1. In still further aspects, the mixture includes plasmid DNA and polyI:C in an about 1:1 ratio (by weight). In further aspects, the cellular adhesion agent is a low- to mid-weight viscosity carboxymethylcellulose. In yet further aspects, the low molecular weight carboxymethylcellulose is present at about 1% to 20% (v/v). In even further aspects, the composition includes complexes of the cationic liposomes and any TRL3 and TRL9 ligands. According to further aspects, the complexes include about 100 ug of the TLR ligands per 1 ml of the 10 mm cationic liposomes. In certain alternative embodiments, the composition also includes an antigen, and the antigen is a viral, bacterial or tumor antigen.

Disclosed herein is a method for inducing innate immune protection in a subject from an infection, including providing to a mucosal surface the subject an effective amount of a composition including: (a) cationic liposomes; (b) a mixture of toll like receptor 3 (TLR3) and toll like receptor 9 (TLR9) ligands; and (c) a cellular adhesion agent. In certain aspects, the subject is a horse, dog or cat. In further aspects, the composition is provided to the subject prior to and/or during boarding. According the further aspects, the subject is selected from a list including of: a horse, dog or cat, a cow, sheep, pig, goat, chicken, and fish. In even further aspects, the infection is a viral or bacterial or fungal or protozoal respiratory infection and where toll like receptor 9 (TLR9) ligand includes a polynucleotide of SEQ ID NO. 1 and the TLR3 ligand includes polyI:C. In certain aspects, the composition is provided to the subject within 24 hours prior to the risk of exposure and within 24 hours to a week or more after exposure, or during the early onset of clinical signs of infection, or during chronic infection. According to even further aspects, providing the composition induces a local, non-specific immune protection against infections at a site of administration, and where the site of administration is selected from a list including of: the reproductive tract, the gastrointestinal tract, the mammary gland, gills, air sacs, eyes, ears, and nose. In yet further aspects, the composition is administered without the concurrent administration of a vaccine.

Further disclosed herein is a method for inducing an immune response to an antigen in a subject, including providing to the subject a composition including: (a) cationic liposomes; (b) a mixture of toll like receptor 3 (TLR3) and toll like receptor 9 (TLR9) ligands; (c) a cellular adhesion agent and the antigen. According to certain aspects, the composition is provided orally, nasally, intravaginally, by uterine or intramammary injection, by aerosol delivery, by delivery in water, or parenterally. In certain further aspects, the subject is a horse, dog or cat.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 13A shows data quantifying the uptake of PCT-01 by nasal lavage cells following intranasal and oral administration in a healthy dog. FIG. 13B shows data quantifying the uptake of PCT-01 by oropharyngeal cells following intranasal and oral administration in a healthy dog.

DETAILED DESCRIPTION

Figure 1:
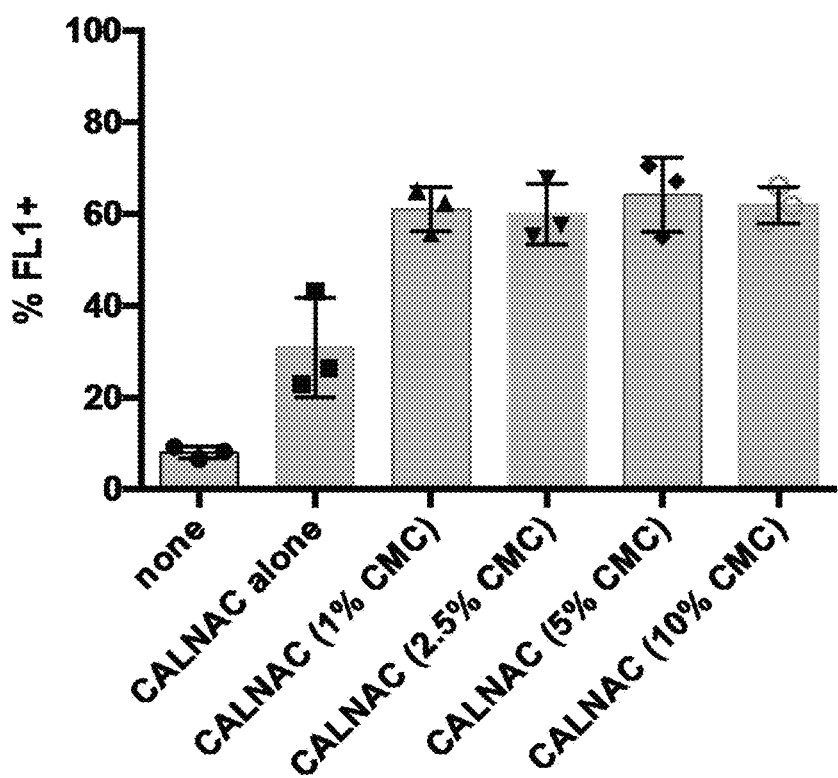
FIG. 1 shows flow cytometric data demonstrating that CMC addition to liposome-TLR3/9 complexes increases adhesion to epithelial cells.

The instant disclosure relates, in part, to improved immunostimulatory compositions, which may be used to induce a non-specific, protective mucosal immune response.

In certain embodiments, the disclosed is an improved immunostimulatory composition designed to stimulate more effective local immune responses at mucosal and epithelial surfaces in the body of a subject. This new invention improves on the immune stimulatory properties of a previously developed immunotherapeutic (cationic-liposome DNA complexes; CLDC) with respect to adhesion to mucosal surfaces, increased potency of immune activation, and duration of immune activation.

The mucosal immune stimulation technology disclosed herein offers a significant improvement over the original CLDC technology, which in itself is a potent immune stimulant. Data provided herein demonstrate superior induction of mucosal immune responses with the compositions of the present invention as compared to previous cationic liposome-DNA complex (CLDC) formulations.

According to certain embodiments, the compositions of the present invention may also be used to induce non-specific immune protection of mammals and birds and other species, e.g., dogs, cats, cattle, horses, swine, chickens, and fish, from viral and bacterial and protozoal infections, as well as infections at other mucosal sites such as the reproductive and GI tract. The compositions may also be used for non-specific protection of mammals, e.g., humans from respiratory viruses such as rhinovirus and influenza or adenovirus, or bacteria such as *Staphylococcus* or *Streptococcus*. In certain embodiments, the composition may be administered as a liquid by the intranasal and oropharyngeal routes to animals, e.g., dogs, cats, cattle, horses, swine, poultry, about 24 h prior to pathogen exposure (eg, shipping to feedlots or boarding facilities or rearing facilities), or within 7 d following exposure to pathogens as a means of inducing local immune protection against early viral or bacterial infections. In a related embodiment, the composition may be used in shelter settings or boarding facilities to protect from or treat feline or canine upper respiratory infections (viral or bacterial). In certain embodiments, the composition may be administered as a an intranasal or oral liquid 24 h prior to entry into boarding or shelter facilities, or administered to animals that may already be exposed or developing signs of infection (eg, therapeutic administration). In a therapeutic setting, the compound would be administered to all animals in a facility, with the treatment repeated again at 7 to 14 day intervals by intranasal and/or oral administration. Also in a therapeutic setting, the compound would be administered to animals or humans with chronic upper respiratory or GI or reproductive tract infections at 7 to 14 day intervals.

In a related embodiment, cattle that are shipped to feedlots would be administered the composition intranasally immediately upon arrival to the facility, and the treatment may be repeated at 7 to 14 day intervals.

In another embodiment, poultry in intensive husbandry settings (eg, broiler operations) that are exposed to pathogens or at risk of exposure are treated with the composition throughout the building by exposure to an aerosol mist generated by an aerosol generator carried as a backpack by facility personnel.

In another embodiment, fish in fish farms or ponds at risk of infection with viral or bacterial or protozoal pathogens would be collected into smaller treatment tanks, and the composition would be diluted in water in the treatment tanks so all the fish would be treated via uptake by the gills or other mucosal surfaces.

In certain embodiments, the composition may be used in humans and administered intranasally, e.g., as a liquid or spray using a spray bottle or similar device. In particular embodiments, humans at risk of contracting viral infections (e.g., during airline travel, holiday gatherings, classrooms) may administer the immune stimulant composition prior to the encounter and then 3 to 7 days afterwards.

The compositions of the present invention generate rapid, broad protection against both viral and bacterial pathogens following application to mucosal surfaces. Data provided herein demonstrate superior induction of mucosal immune responses with the compositions of the present invention as compared to previous cationic liposome-DNA complex (CLDC) formulations.

According to certain alternative embodiments, the instant disclosure also relates, in part, to improved immunostimulatory compositions, which may be used as adjuvants in combination with antigens in vaccines. In certain embodiments, disclosed is an improved liposomal vaccine adjuvant with greater lymph node trafficking ability for greater vaccine adjuvant activity. By incorporating a an adhesive agent (e.g., carboxymethylcellulose) with a cationic liposome-TLR agonist complex, migration of vaccine antigens to draining lymph nodes is enhanced, resulting in enhanced vaccine responses. This new invention improves on the immune stimulatory properties of a previously developed immunotherapeutic (cationic-liposome DNA complexes; CLDC), particular with respect to vaccine adjuvant properties.

Illustrative embodiments of these and other aspects of the invention are described in further detail below. However, the invention is not limited to these specific embodiments.

General Methods

The practice of the present invention will employ, unless otherwise indicated, conventional techniques of cell culturing, molecular biology (including recombinant techniques), microbiology, cell biology, biochemistry and immunology, which are within the skill of the art. Such techniques are explained fully in the literature, such as, Molecular Cloning: A Laboratory Manual, third edition (Sambrook et al., 2001) Cold Spring Harbor Press; Oligonucleotide Synthesis (P. Herdewijn, ed., 2004); Animal Cell Culture (R. I. Freshney), ed., 1987); Methods in Enzymology (Academic Press, Inc.); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Manual of Clinical Laboratory Immunology (B. Detrick, N. R. Rose, and J. D. Folds eds., 2006); Immunochemical Protocols (J. Pound, ed., 2003); Lab Manual in Biochemistry: Immunology and Biotechnology (A. Nigam and A. Ayyagari, eds. 2007); Immunology Methods Manual: The Comprehensive Sourcebook of Techniques (Ivan Lefkovits, ed., 1996); Using Antibodies: A Laboratory Manual (E. Harlow and D. Lane, eds., 1988); and others.

Definitions

Unless defined otherwise, all technical and scientific terms used herein have the same meaning as commonly understood by those of ordinary skill in the art to which the invention belongs.

As used herein, the term "effective amount" refers to at least an amount effective, at dosages and for periods of time necessary, to achieve the desired result, e.g., enhance innate immune response, an enhanced immune response to an antigen. An effective amount can be provided in one or more administrations.

As used herein, the term "subject" or "individual" refers to the target of administration, e.g. an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. In one aspect, the subject is a mammal. e.g., a human, a companion animal (e.g., dog, cat, rodent, rabbit, etc.), a sport animal (e.g., horse, dog, bull, etc.), a farm or food animal (e.g., pig, cow, sheep, goat, etc.), livestock (e.g., donkeys, goats, guinea pigs, sheep, cattle, llamas, etc.), or any other mammalian veterinary animal, or to a bird (eg, chicken, turkey, duck) or any other avian veterinary species, or other non-mammalian species such as farm-reared fish, or other species such as reptiles or amphibians.

As used herein, the singular form "a", "an", and "the" includes plural references unless indicated otherwise.

Reference to "about" a value or parameter herein refers to the usual error range for the respective value readily known to the skilled person in this technical field. In particular embodiments, reference to about refers to a range within 10% higher or lower than the value or parameter, while in other embodiments, it refers to a range within 5% or 20% higher or lower than the value or parameter. Reference to "about" a value or parameter herein includes (and describes) aspects that are directed to that value or parameter per se. For example, description referring to "about X" includes description of "X."

As used herein, the term "modulating" means changing, and includes positive modulating, such as "increasing," "enhancing," "inducing" or "stimulating," as well as negative modulating such as "decreasing," "inhibiting" or "reducing," typically in a statistically significant or a physiologically significant amount as compared to a control. An "increased," "stimulated" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no treatment as described herein or by a control treatment, including all integers in between. A "decreased," "inhibited" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%), 80%, 85%, 90%, 95%, or 100% decrease in the amount produced by no treatment as described herein or by a control treatment, including all integers in between.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

It is understood that aspects and embodiments of the invention described herein include "comprising," "consisting," and "consisting essentially of" aspects and embodiments.

As used herein, the term "adjuvant" has its conventional meaning, i.e., the ability to enhance the immune response to a particular antigen. Such ability is manifested by a significant increase in immune-mediated protection. An enhancement of humoral immunity is typically manifested by a significant increase (usually >10%) in the titer of antibody raised to the antigen. Similarly, enhancement of cellular immunity is typically manifested by a significant increase (usually >10%) in the number of responding CD8+ or CD4+ T cells. The term "about" in relation to a numerical value x means, for example, x+/−10%.

As used herein, the terms "optional" or "optionally" means that the subsequently described event or circumstance can or cannot occur, and that the description includes instances where said event or circumstance occurs and instances where it does not.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s). In particular embodiments, an antigen is administered concurrently with a composition of the present invention.

The terms "cancer" and "cancerous" refer to or describe the physiological condition in mammals that is typically characterized by unregulated cell growth. Included in this definition are benign and malignant cancers as well as dormant tumors or micrometastases. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; and post-transplant lymphoproliferative disorder (PTLD), as well as abnormal vascular proliferation associated with phakomatoses, edema (such as that associated with brain tumors), and Meigs' syndrome.

"Poly(I:C)" (polyinosinic-polycytidylic acid) is recognized by TLR3 inducing the activation of NF-kB and the production of cytokines. Poly(I:C) is composed of a strand of poly(I) annealed to a strand of poly(C). The size of the strands varies. InvivoGen and other manufacturers provide poly(I:C) with at least 2 different sizes:
Poly(I:C) (HMW) with a high molecular weight has an average size of 1.5-8 kb, and Poly(I:C) (LMW) with a low molecular weight has an average size of 0.2-1 kb.

"CpG oligodeoxynucleotides" (CpG ODN; CpG oligos) are short single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. When these CpG motifs are unmethylated, they act as immunostimulants CpG motifs are considered pathogen-associated molecular patterns (PAMPS) due to their abundance in microbial genomes but their rarity in vertebrate genomes. The CpG PAMP is recognized by the pattern recognition receptor (PRR) Toll-Like Receptor 9 (TLR9), in mammals and avian and fish species.

As used herein, PCT-01 is a complex solution comprised of cationic liposomes, non-coding plasmid DNA, polyinosinic-polycytidylic acid, and carboxymethylcellulose in an appropriate diluent for in vitro and in vivo studies.

Non-coding plasmid DNA consists of bacterial replication elements in a circular arrangement. The DNA in plasmids, because it is produced in bacteria, is relatively unmethylated compared to mammalian DNA, and can act as an immunostimulant recognized by the pattern recognition receptor (PRR) Toll-Like Receptor 9 (TLR9), which is expressed in mammals and avian species. In addition, these non-coding plasmids can be engineered to overexpress CpG motifs. In the case of the current invention, the plasmid does not code for any known mammalian genes, and instead consists of several "islands" of CpG motifs (oligonucleotides) engineered into the plasmid to increase its immune stimulatory properties. "CpG oligodeoxynucleotides" (CpG ODN; CpG oligos) are short single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. When these CpG motifs are unmethylated, they act as immunostimulants CpG motifs are considered pathogen-associated molecular patterns (PAMPS) due to their abundance in microbial genomes but their rarity in vertebrate genomes. The CpG PAMP is recognized by the pattern recognition receptor (PRR) Toll-Like Receptor 9 (TLR9), in mammals and avian species.

Immunostimulatory Compositions

The instant disclosure provides novel immunostimulatory compositions. In certain embodiments, these immunostimulatory compositions are used to induce a non-specific immune response.

In particular embodiments, the immunostimulatory compositions comprise or consist of the following components:
1. cationic liposomes comprised of a cationically-charged lipid in a fixed ratio with cholesterol;
2. one or more TLR3 and/or TLR9 ligands or agonists (TLR ligands), including non-coding plasmid DNA (TLR9 agonist) and polyinosinic-polycytidylic acid (TLR3 agonist); and
3. a cellular adhesion agent (e.g.,carboxymethyl cellulose, or chitosan, polyglycol, or hyaluronan).

In particular embodiments, the immunostimulatory contains both a CLDC and a cellular adhesion agent. In particular embodiments, the immunostimulatory composition contains both a CLDPC and a cellular adhesion agent.

TLR3 and TLR9 Ligands (TLR Ligands)

Figure 34:
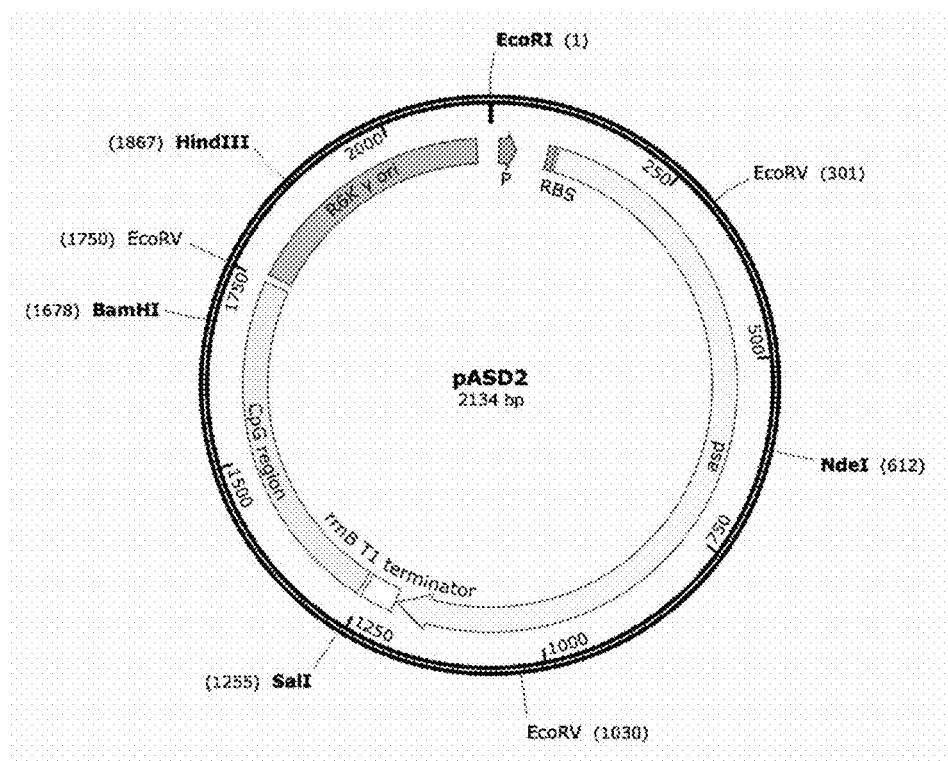
FIG. 34 shows a plasmid map of a TLR9 agonist, according to certain embodiments.

In one embodiment, the TLR ligand is a cationic liposome combined with a TLR9 agonist (either plasmid DNA (e.g., non-coding plasmid DNA), or CpG oligos), known as a CLDC adjuvant. In one embodiment, the TLR ligand is a cationic liposome DNA-pIC complex (CLDPC). According to certain exemplary embodiments, the TLR9 agonist is a non-coding plasmid comprising SEQ ID NO. 1. In these embodiments, the plasmid (as seen in FIG. 34) comprises a plurality of CpG motifs, and also does not contain antibiotic resistance genes (as mandated for regulatory purposes by the USDA and FDA).

The compositions of the present invention may elicit both a cell-mediated immune response and a humoral immune response. In certain embodiments, this immune response will induce long lasting antibodies plus a T cell-mediated immune response, which could involve CD4 or CD8 T cells, or both. The CLDC adjuvant primarily elicits a Th1 response. In particular embodiments, the TLR ligand is prepared from CLDC adjuvant and/or CLDPC adjuvant capable of eliciting effective cell-mediated immunity. In certain embodiments, the compositions may include other adjuvants capable of eliciting Th1 immune responses.

In particular embodiments, the TLR ligand comprises or consist of cationic liposomes complexed to non-coding plasmid DNA (CLDC), as this adjuvant is particularly effective in eliciting T cell (both CD8 and CD4) responses. The CLDC adjuvant can also be prepared using cationic liposomes admixed with CpG oligos. In particular embodiments, the CLPDC includes cationic liposomes complexed to polyI:C and plasmid DNA. In certain embodiments, the complex includes cationic liposomes (e.g., DOTAP) in a 1:1 to 1:2 molar ratio with cholesterol, e.g., formulated as small unilamellar vesicles in dextrose or sucrose solution, and polyI:C and/or plasmid DNA (e.g., non-coding DNA). When both are present, in certain embodiments, the polyI:C and plasmid DNA may be present in a ratio of 1:2 to 2:1, e.g., 1:1 (by weight). In certain embodiments, the complex contains about 10 µg to about 500 µg, about 50 µg to about 200 µg or about 100 µg total of pIC and/or DNA per 1 ml liposomes. The liposome concentration in this embodiment would be 10 mM. In other embodiments, the cationic liposomes are comprised of a cationic lipid (e.g., DOTAP or DOTIM) mixed with a 1:1 molar ratio of cholesterol and rehydrated to produce liposomes in the range of 250 nm diameter (see, e.g., Dow, S. W. et al., J Immunol, 1999, 163:1552-1561; Zaks, K. et al., J Immunol, 2006, 176:7335-7345; Mitchell, L. A. et al., J. Immunology, 2012, 189; and Dow et al., Liposome Adjuvant Review, 2007). In particular embodiments, any of the CLDC and CLPDC adjuvants also include a cellular adhesive agent, such as carboxymethyl cellulose.

In certain embodiments, the CLDC adjuvant comprises: cationic liposomes (e.g., DOTAP and cholesterol (10 mM), 1:2 to 2:1 ratio or about 1:1 ratio), and non-coding plasmid DNA (10 µg/ml to 500 µg/ml or 10 µg/ml to 200 µg/ml, or about 50 µg/ml). In particular embodiments, the CLDC adjuvant comprises cationic liposomes (e.g., DOTAP and cholesterol, 1:1 ratio), and non-coding plasmid DNA (50 µg/ml). In particular embodiments, the compositions include both a CLDC adjuvant and carboxymethyl cellulose (CMC) at 1% to 20%, 2% to 15%, 2.5% to 10%, 5% or 10% or about 5% v/v.

In certain embodiments, the CLPDC adjuvant comprises: cationic liposomes (e.g., DOTAP and cholesterol, 1:2 to 2:1 ratio or about 1:1 ratio), non-coding plasmid DNA (10 ug/ml to 500 ug/ml or 10 ug/ml to 200 ug/ml, or about 50 ug/ml), and synthetic pIC (10-500 ug/ml or 10-200 ug/ml or about 50 ug/ml). In particular embodiments, the LPDC composition comprises cationic liposomes (e.g., DOTAP and cholesterol, 1:1 ratio), non-coding plasmid DNA (50 ug/ml), and synthetic pIC (50 ug/ml). In particular embodiments, the compositions includes both a CLPDC composition and carboxymethyl cellulose (CMC) at 1% to 20%, 2% to 15%, 2.5% to 10%, 5% or 10% or about 5% v/v with the final composition.

Cellular Adhesion Agent

In certain embodiments, the composition or adjuvant contains a cellular adhesion agent, which may enhance uptake the composition. Disclosed when administered either orally or nasally, adheres to and/or anchors to a subject's mucous membrane for a period of time sufficient for the composition to exert its immunostimulatory effects.

In particular embodiments, the cellular adhesion agent is carboxymethyl cellulose, e.g. a low to mid-weight viscosity formulation. Carboxymethyl cellulose (CMC) or cellulose gum is a cellulose derivative with carboxymethyl groups (—CH2-COOH) bound to some of the hydroxyl groups of the glucopyranose monomers that make up the cellulose backbone. It is often used as its sodium salt, sodium carboxymethyl cellulose. In particular embodiments, CMC is present in the composition at 1% to 20% (v/v), 2% to 15%, 2.4% to 10%, or about 5% (v/v). In particular embodiments of low viscosity carboxymethylcellulose (CMC), the viscosity of a 4% solution in water at 25° C. is 50-200 centipoise (cps). The viscosity is both concentration and temperature dependent. As the temperature increases, the viscosity decreases. As the concentration increases, the viscosity increases. In various embodiments, low, medium and high viscosity carboxymethylcellulose (CMC) are used in the compositions of the present invention. Low viscosity CMC is usually used in "thin" aqueous solutions. Medium viscosity CMC is usually used to make solutions that look like a syrup. In particular embodiments, low viscosity CMC has a molecular weight of about 90 kDa; a degree of polymerization of 400; a degree of substitution of 0.65-0.90 (6.5-9.0 carboxymethyl groups per 10 anhydroglucose units); and a sodium content of about 8% by weight. In particular embodiments, medium viscosity carboxymethylcellulose (CMC) has a viscosity of a 2% solution in water at 25° C. of 400-800 centipoise (cps). The viscosity is both concentration and temperature dependent. As the temperature increases, the viscosity decreases. As the concentration increases, the viscosity increases. In particular embodiments, medium viscosity CMC has a molecular weight of about 250 kDa; a degree of polymerization of about 1100; and a degree of substitution of about 0.7 (approximately 7 carboxymethyl groups per 10 anhydroglucose units). In particular embodiments, high viscosity carboxymethylcellulose (CMC) has a viscosity of a 1% solution in water at 25° C. is 1500-3000 centipoise (cps). The viscosity is both concentration and temperature dependent. As the temperature increases, the viscosity decreases. As the concentration increases, the viscosity increases. In particular embodiments, high viscosity CMC is used to make a mixture that resembles a cream or lotion. In certain embodiments, low viscosity CMC is used in "thin" aqueous solutions. In particular embodiments, high viscosity CMC has a molecular weight of about 700 kDa; a degree of polymerization of 3200; and a degree of substitution of about 0.65-0.85 (6.5-8.5 carboxymethyl groups per 10 anhydroglucose units). As used herein, a "poise" is a unit of viscosity based on a flow rate using the standard of water at 20° C. having a poise value of exactly 1 centipoise or one hundredth of a poise. One poise may be defined as "P" in the following equation: $1\ P=(0.10\ kg/meter)/sec=(1\ g/cm)/sec$.

According certain alternative embodiments, the cellular adhesion agent is chitosan. In further alternative embodiments, the cellular adhesion agent is hyaluronan. Hyaluronan, also known as hyaluronic acid, is a is an anionic, nonsulfated mucoid polysaccharide of biological origin. According to still further embodiments, the cellular adhesion agent is a polymer. As will be appreciated by those skilled in the art, suitable polymers in these embodiments are those with hydrophilic functional groups or those that bind to specific receptors on cell or mucus surface (eg, lectins, thiolated polymers) or lipoid S100.

In certain embodiments, the cellular adhesion agent is a propylene glycol. As used herein, "propylene glycol" or "PEG" is a polyether compound of general formula H—(O—CH2-CH2)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. In certain embodiments, the PEG is water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Suitable PEG polymers will vary substantially by weights ranging from about 200 to about 60,000. In certain embodiments, PEGs having molecular weights from 200 to 2,000 or from 200 to 500 are used. Lower-molecular-weight PEGs are also available as pure oligomers, referred to as monodisperse, uniform, or discrete. These are used in certain embodiments of the present invention. PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear.

In one embodiment, the composition is prepared by preparing complexes of cationic liposomes with DNA and/or pIC. The adhesive agent (also referred to as the cellular adhesive agent) is then added to the combined complexes. In particular embodiments, an antigen is added to the combined complexes and cellular adhesive agent. In particular embodiments, the composition is administered by a variety of mucosal routes of delivery, including intranasally, orally, intrarectally, intravaginally, or by the intramammary or intra-uterine route, or by aerosol mist exposure, or by dilution in water (fish). Alternative routes of delivery include parenterally, e.g., intravenously, subcutaneously, intraperitoneally, or intramuscularly.

Immune cells at mucosal surfaces include dendritic cells (DC), monocytes and macrophages, neutrophils, and B cells, and in some species such as cattle and other ruminants, a specialized subset of T cells known as gamma-delta T cells (γδ T cells). In addition, epithelial cells lining mucosal surfaces can also respond to immune stimuli. The coordinated activation of immune cells and epithelial cells can induce immune responses to suppress infection by either prevent viral or bacterial infection, or significantly reduce the severity of infection and limit pathogen replication. In addition, strong activation of local immune responses at mucosal surfaces can also reduce the severity of infection even after the infection has already been initiated (ie, when the immune stimulus is administered in an early therapeutic setting as opposed to for prophylaxis).

When immune stimuli reach mucosal surfaces, they are sampled by local DC and macrophages, which then become activated and produce cytokines and chemokines, including inflammatory cytokines (TNF, IL-1, IL-6) as well as antiviral and antibacterial cytokines (IFN-g, IFN-a, INF-b) and other cytokines such as IL-12 and IL-22. The epithelial cells also respond to immune stimuli and produce chemokines (and cytokines) that serve to recruit immune cells to the sites of inflammation. Key chemokines produced by epithelial cells include MCP-1, which recruits monocytes, and IL-8, which recruits neutrophils. Monocytes and neutrophils both play key role in early immune defenses against viral and bacterial pathogens of the respiratory tract and other mucosal surfaces. Some immune stimuli can also directly activate a specialized type of T cell (γδ T cell) that is only found at mucosal surfaces, especially in cattle and other ruminants, and also another cell type known as NK cells, which are present in all mammalian species.

The early cytokine and chemokine responses serve to amplify local immune responses and recruit other inflammatory cells, including monocytes, neutrophils, NK cells and later conventional T cells. These other inflammatory cells produce antiviral and antibacterial cytokines, and also secrete factors such as reactive oxygen and reactive nitrogen species that can directly kill certain bacteria and viruses. In addition, these immune cells and epithelial cells can also produce antimicrobial peptides that kill bacteria and enhance the activity of antibiotics.

To activate mucosal immune defenses effectively, an immune stimulant needs several important properties. These include the ability to first adhere well to epithelial surfaces, and in some cases penetrate into and around epithelial cells. Cationic liposomes are very effective at introducing nucleic acid molecules such as polyIC and plasmid DNA or CpG oligonucleotides into cells such as epithelial cells and immune cells.

An effective mucosal immune stimulant also needs to be very potent, given the large surface areas that must be contacted by relatively small volumes of the immune stimulant. In addition, the ability to induce broad spectrum immune responses, by activating both antibacterial and antiviral immune pathways, is important. Thus, activation of the TLR3 pathway induces anti-viral immune responses, while activation of the TLR9 pathway induces antibacterial immune responses. By activating both pathways simultaneously, the breadth and potency of the immune response that is induced is greatly increased.

An effective mucosal immune stimulant must also be capable of interacting with epithelial cells and immune cells for prolonged periods of time in order to induce a sustained immune response. Thus, addition of a mucosal adhesion agent serves to disperse the immune stimulant over large mucus membrane surfaces, and also prolongs the contact time. For example, addition of a mucosal adhesion agent such as carboxymethylcellulose to an immune stimulant such as a liposome-TLR agonist complex can induce local immune stimulation at mucosal surfaces for more than 7 to 14 days. This period of time is sufficient for protection from most pathogen exposures in respiratory disease settings. Importantly, from the standpoint of treatment with mucosal immune stimulants, this prolonged duration of immune activation can generate much more effective long-term therapeutic responses, and can in some cases also result in the generation of T cell responses and antibody responses (as described further below).

Vaccine and Adjuvants

In certain alternative embodiments, the present invention includes a vaccine that comprises an immunostimulatory compositions disclosed herein and an antigen. In these embodiments, all components of the adjuvant or vaccine are present in the same pharmaceutical composition, which may be a liquid composition and which may further comprise one or more excipients, diluents or carriers. The pharmaceutical compositions may be sterile. In certain embodiments, the liposome-TLR ligand complexes comprise a vaccine adjuvant.

In certain embodiments, this aspect includes a immunostimulant that comprises or consists of cationic liposomes complexed to TLR agonists (plasmid DNA and/or polyinosinic polycytidylic acid; pIC), and low- or medium-molecular weight carboxymethylcelluose (CMC) as an adhesive agent to increase uptake and trafficking to lymph nodes. In one embodiment, they comprise or consist of: 1) cationic liposomes (e.g., DOTAP and cholesterol, 1:1 molar ratio); 2) non-coding plasmid DNA (e.g., 50 ug/ml); 3) synthetic pIC (e.g., 50 ug/ml); 4) carboxymethylcellulose (CMC) (e.g., 5% v/v with final vaccine).

In one embodiment, to prepare the adjuvant, complexes of cationic liposomes with DNA and pIC are prepared, then the vaccine antigen is added. The final step is the addition of the CMC adhesive agent. In particular embodiments, the vaccine is then administered by the s.c. or i.m. route. In various embodiments, this vaccine technology is applicable to the treatment and prevention of both infectious disease and cancer vaccine applications.

For generation of vaccine immunity with vaccine adjuvants and antigens, there are two important categories of T cells. While these T cells play little direct role in mucosal immune responses, they are important for longer term protection from viral and bacterial infections, as in the case of conventional prophylactic vaccines. These T cells also play an important role in cancer immunity.

Two types of T cells, CD4 and CD8 cells, initiate and/or enhance cell mediated immunity and humoral immunity. CD8 T cells interact with antigens displayed on MHC Class I molecules. CD4 T cells recognize antigenic peptides bound to MHC class II molecules. Upon interaction with a MHC class II molecule, the CD4 cells secrete factors such as cytokines, which activate B cells, cytotoxic T cells, macrophages, and other cells that participate in an immune response.

Other Adjuvants

Other adjuvants may be present in the adjuvant compositions and vaccines of the present invention, or delivered in combinations with an adjuvant or vaccine of the present invention, including those that stimulate either or both a TH1 and/or TH2 response. TH1 adjuvants suitable for use in the invention may include, for example, saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are typical TH1 adjuvants. TH2 adjuvants suitable for use in the invention include, for example, mineral containing compositions, oil-emulsions, and ADP-ribosylating toxins and detoxified derivatives thereof. Mineral containing compositions, such as aluminum salts are typical TH2 adjuvants for use in the invention.

Other adjuvants that may be present in the compositions/adjuvants of the present invention include any adjuvant known or used in the art, including but not limited to: CLDC adjuvants, mineral salts, such as aluminum salts and calcium salts, including hydroxides (e.g., oxyhydroxides), phosphates (e.g., hydroxyphosphates, orthophosphates) and sulphates, etc.; oil-in-water emulsions, such as squalene-water emulsions, including MF59 (5% Squalene, 0.5% Tween 80, and 0.5% Span 85, formulated into submicron particles using a microfluidizer); complete Freund's adjuvant (CFA) and incomplete Freund's adjuvant (IFA); saponin formulations, such as QS21 and ISCOMs; virosomes and virus-like particles (VLPs); bacterial or microbial derivatives, such as non-toxic derivatives of enterobacterial lipopolysaccharide (LPS), Lipid A derivatives; immunostimulatory oligonucleotides, such as IC-31 (deoxynucleotide comprising 26-mer sequence 5'-(IC)13-3' and polycationic polymer polypeptide comprising an 11-mer amino acid sequence KLKLLLLLKLK SEQ ID NO:2)) and ADP-ribosylating toxins and detoxified derivatives thereof; human immunomodulators, including cytokines, such as interleukins (e.g., IL-1, IL-2, IL-4, IL-5, IL-6, IL-7, IL-12, interferons (e.g., interferon-gamma), macrophage colony stimulating factor, and tumor necrosis factor; bioadhesives and mucoadhesives, such as chitosan and derivatives thereof, esterified hyaluronic acid microspheres or mucoadhesives, such as cross-linked derivatives of poly(acrylic acid), polyvinyl alcohol, polyvinyl pyrollidone, polysaccharides and carboxymethylcellulose; microparticles (e.g., a particle of about 100 nm to about 150 um in diameter) formed from materials that are biodegradable and non-toxic (e.g., a poly (alpha-hydroxy acid), a polyhydroxybutyric acid, a polyorthoester, a polyanhydride, a polycaprolactone, etc.); liposomes; polyoxyethylene ethers and polyoxyethylene esters; PCPP formulations; muramyl polypeptides, including N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-iso glutaminyl-1- alanine-2-(1'-2'-dip almito yl-s-n-glycero-3-hydroxyphosphoryloxy)-ethylamine MTP-PE); and imidazoquinolone compounds, including Imiquamod and its homologues (e.g. "Resiquimod 3M"). Illustrative adjuvants suitable for use include, but are not limited, to cationic lipid DNA complexes (CLDC), CpG-oligonucleotides, poly I:C, LPS, alpha-galactosylceramide, and the like.

Antigens

In particular embodiments, the adjuvant compositions of the present invention comprise or are used in combination with an antigen, and in certain embodiments, the vaccines of the present invention comprise an antigen. In certain embodiments, the antigen is a viral or bacterial antigen. In certain embodiments, compositions (e.g., vaccines) and kits of the invention include an antigen, and certain methods of the invention comprise administering an antigen. In certain embodiments, the antigen present in the vaccine compositions provided by the invention can be any material or substance that can induce an immune response (i.e., cellular and/or humoral immune response) by the immune system of a human or animal. For example, the antigen can be a polypeptide of interest derived from an infectious agent, e.g., a bacterium, a virus, a fungus, a protozoan, a parasite, or a prion. The antigen can be a whole microbe or a mixture thereof. The compositions can include a live whole infectious agent. In certain embodiments, the compositions can include a killed or inactivated (attenuated) infectious agent.

In certain embodiments, the antigen comprises, e.g., a polypeptide, nucleic acid, polysaccharide, a fatty acid or the like, derived from an infectious agent. In certain embodiments, the antigen can be a subunit or fragment of a polypeptide, or a fragment of a nucleic acid or polysaccharide derived from an infectious agent. In certain embodiments, the antigen is a recombinant polypeptide produced in a heterologous expression system, e.g., a recombinant protein derived from an infectious agent that was expressed in and purified from cells of another organism. However, an antigen can also be a recombinant nucleic acid construct which encodes a polypeptide antigen of interest (e.g., an expression construct). The antigen can comprise a viral subunit, a virus-like particle, a capsular (poly) saccharide; a bacterial outer membrane bleb formation containing one or more of bacterial outer membrane proteins, a phospholipid, a lipopolysaccharide, or a polysaccharide.

In certain embodiments, the antigen can be a naturally occurring substance. In certain embodiments, the antigen comprises or is derived from an allergen, e.g., pollen. In certain embodiments, the antigen comprises or is derived from a toxin. In certain embodiments, the antigen comprises or is derived from an addictive substance, including, without limitation, nicotine, caffeine, alcohol, and the like. In certain embodiments, the antigen can be a non-naturally occurring (i.e., synthetic) substance, e.g., a synthetic peptide, a synthetic polysaccharide, or a synthetic polymer.

In certain embodiments, the antigen is a tumor cell or is derived from a tumor cell, including cells from any of the types of cancers or tumors described herein.

In certain embodiments, the antigen can be provided in a vaccine, e.g., any vaccine known in the art. The vaccine can be a nucleic acid construct (e.g., a DNA vaccine). The vaccine can be a viral vector vaccine, which uses live viruses to carry DNA into an individual's cells. The DNA contained in the viral vaccine encodes antigen(s) that, once expressed in the infected cells, elicit an immune response. Alternatively, the vaccine can be a subunit vaccine, e.g., a specific protein from a virus. The vaccine can be a dendritic cell vaccine, in which an individual's dendritic cells are cultured with an antigen and then reinjected into the individual to stimulate an immune response. In certain embodiments, the vaccine can be a monovalent vaccine, i.e., containing a single antigen. In certain embodiments, the vaccine containing the antigen is a polyvalent or multivalent vaccine, i.e., containing more than one antigen.

The amount of antigen to be included in the vaccines and used in the methods of the present invention (i.e., any of the methods described herein) will depend on the immunogenicity of the antigen itself and the efficacy of any adjuvants co-administered therewith. In general, an immunologically effective dose comprises between about 1 μg to about 1000 μg of the antigen, preferably between about 5 μg to about 500 μg, more preferably between about 10 μg to about 200 μg. In some embodiments, an immunologically effective dose can be at least about 1μ, at least about 5 μg, at least about 10 μg, at least about 25 μg, at least about 50 μg, at least about 100 μg, at least about 150μ, at least about 200 μg, at least about 250 μg, at least about 300 μg, at least about 350μ, at least about 400 μg, at least about 450 μg, at least about 500 μg, at least about 550 μg, at least about 600 μg, at least about 650 μg, at least about 700 μg, at least about 750 μg, at least about 800 μg, at least about 850 μg, at least about 950 μg, or up to about 1000 μg of antigen. In embodiments where the antigen is a recombinant protein or peptide, a suitable dose can be about 10-100 μg. In embodiments where the antigen is a recombinant protein or peptide, a suitable dose can be about 10-100 μg.

Pharmaceutical Compositions

The present invention includes pharmaceutical compositions comprising a composition designed for mucosal immune stimulation. In this embodiment, the composition consists of a liquid immune stimulant, formulated with a pharmaceutically acceptable carrier, diluent or excipient. The proposed compositions may thus be pharmaceutically acceptable. Such diluents, excipients and carriers are known and available in the art. Compositions may be in an aqueous form. In the most desirable formulation, the immune stimulant would be prepared as a stable liquid (during refrigeration) in an acceptable carrier. In other instances, the immune stimulants may be lyophilized during manufacture, to be reconstituted later into an aqueous form at the time of use. Thus a composition of the invention may be liquid or dried, such as a lyophilized formulation. The most preferred formulation is as a stable liquid formulation.

In other embodiments, the composition further comprises a vaccine, which may further comprise one or more pharmaceutically acceptable carrier, diluent or excipient. Compositions may thus be pharmaceutically acceptable. Such diluents, excipients and carriers are known and available in the art. Compositions may be in an aqueous form. Alternatively, e.g., prior to administration, the composition may have been in a non-aqueous form. For instance, although some vaccines are manufactured in aqueous form, then filled and distributed and administered also in aqueous form, other vaccines are lyophilized during manufacture and are reconstituted into an aqueous form at the time of use. Thus a composition of the invention for vaccination may be liquid or dried, such as a lyophilized formulation.

In certain embodiments, pharmaceutical compositions of the present invention are formulated for delivery by a variety of mucosal routes of delivery, including intranasally, orally, intrarectally, intravaginally, or by the intramammary or intra-uterine route, or by aerosol mist exposure, or by dilution in water (fish). Alternative routes of delivery include parenterally, e.g., intravenously, subcutaneously, intraperitoneally, or intramuscularly.

Kits

The composition may be present in one or more containers or vials, e.g., single use or multiuse containers or vials. The multiuse vials may contain a rubber diaphragm suitable for retrieving multiple doses of the immune stimulant. The composition may also be supplied in flexible plastic bags that can be connected to multi-dose intranasal syringes, as in a feedlot operation. The composition may also be further diluted in a suitable diluent for administration in an aerosol delivery device that can be worn as a backpack for administration to poultry, or in a dispensing device suitable for delivery into water for treatment of fish.

The composition may also present in a kit comprising a container with the immunostimulatory composition. The composition may be present in a kit comprising a container comprising the immunostimulatory composition, along with a delivery device. In various embodiments, the kit or composition may include material for a single treatment, or may include material for multiple treatments (i.e., a "multidose" kit). As an alternative (or in addition) to including a preservative in multidose compositions, the compositions may be contained in a container having an aseptic adaptor for removal of material. In a related embodiment, the present invention includes a kit comprising the composition of the present invention and a syringe. In certain embodiments, the syringe comprises a bulb tip or other delivery tip. In certain embodiments, the syringe may be used to or is adapted for use to deliver the composition to the nasal cavity, oral cavity and/or pharyngeal region of a mammal. In certain embodiments, the animal is a mammal (horse, dog, cat, bovine, swine, sheep, goat) or avian (chicken, turkey, duck) or fish (e.g., talapia, salmon, trout, catfish).

Methods of Treatment—Stimulation of Innate Immune Response

The instant disclosure includes methods of inducing an immune response, e.g., a non-specific immune response by providing a composition of the present invention to a subject in need thereof. In certain aspects, the composition is administered in a therapeutically effective amount. In further aspects, the composition is administered in a prophylactically effective amount. In exemplary embodiments, doses for treatment of cattle would be in the range of 1 ml to 5 ml of PCT-01 administered into each nostril, for goats and sheep, 0.5 ml to 3 ml PCT-01 in each nostril, for dogs 0.1 ml to 3 ml PCT-01 in each nostril (and 1 ml to 5 ml orally), for cats 0.1 ml to 2 ml PCT-01 in each nostril and 0.5 to 3 ml orally. For treatment of poultry, an example dose would be 1 to 100 ml PCT-01 diluted in 100 to 1000 ml of suitable diluent (eg, saline, D5W) and administered as an aerosol to treat a 30 by 30 foot room with 100 chickens. For treatment of fish, and example dose would be 1 to 50 ml PCT-01 diluted in 1000 to 10,000 gallons of water for 24 h of treatment. In humans, the intranasal dose of PCT-01 would be 0.1 to 2 ml administered in each nostril.

In particular embodiments, the subject is a mammal at risk of infection with an infectious agent (or already infected with such an agent), such as a virus or bacterium, or a mammal that has already been recently infected. Examples include but are not limited to: 1) prevention or early treatment of kennel cough in dogs, or upper respiratory tract infection syndrome in cats; 2) prevention or early treatment of bovine respiratory tract disease (BRD) syndrome in cattle (beef or dairy); 3) prevention or early treatment of respiratory tract disease in swine, sheep, or goats; 4) intra-mammary infusion for prevention or treatment of mastitis in cattle; 5) intra-uterine infusion for prevention or early treatment of metritis in cattle or horses; 6) oral administration for treatment of inflammatory bowel disease in dogs, cats, humans; and 7) intra-nasal administration for prevention or early treatment of viral upper airway infections in humans.

In another embodiment, the subject is a bird at risk of infection, or already having undergone recent infection. Examples include but are not limited to prevention or treatment of viral or bacterial respiratory tract infections (eg, influenza infection) in poultry (chickens, turkeys, ducks) in intensive rearing conditions (eg, boiler operations, egg laying facilities). In addition, the composition could be directly administered to eggs (in ovo) for induction of innate immune responses in the developing embryo to improve hatchability and early resistance to infection.

In another embodiment, the subject is fish at risk of infection, or already having undergone recent infection. Examples include but are not limited to prevention or treatment of viral or bacterial or protozoal infections in fish in intensive fish rearing facilities. Examples include but are not limited to fish in aquaculture settings (eg, talapia, trout, salmon, catfish), where the composition would be administered by diluting in water in small treatment ponds or tanks for periods of several hours of days of treatment.

In certain embodiments, the composition is provided by a variety of mucosal routes of delivery, including intranasally, orally, intrarectally, intravaginally, or by the intramammary or intra-uterine route, or by aerosol mist exposure, or by dilution in water (fish). Alternative routes of delivery include parenterally, e.g., intravenously, subcutaneously, intraperitoneally, or intramuscularly.

According to certain embodiments, administration of the composition is applied to a mucosal surface. According to certain exemplary embodiments, the composition is applied topically to the nose, mouth, upper airways, air sacs, gills, ears, eyes, uterus, mammary gland, and or gastrointestinal tract.

The present invention includes methods of inducing an immune response, e.g., an immune response specific to an antigen, by providing a composition (e.g., a non-specific immune stimulant) of the instant disclosure to a subject in need thereof. In particular embodiments, the subject is a mammal at risk of infection with an infectious agent, or shortly after infection with, an agent such as a virus or bacterium or a protozoal agent or a fungus.

Particular embodiments include methods of treating or preventing an infection, e.g., a viral or bacterial or protozoal infection, including respiratory tract infections by administering to a subject in need thereof an effective amount of the composition.

Methods of Treatment—Stimulation of Antigen-Specific Immune Response According to certain alternative embodiments, disclosed are methods of inducing an immune response, e.g., an immune response specific to an antigen, by providing a composition (e.g., a vaccine composition) of the present invention to a subject in need thereof. In particular embodiments, the subject is a mammal at risk of exposure to an infectious agent, such as a virus or bacterium.

Particular embodiments include methods of treating or preventing an infection, e.g., a viral or bacterial infection, including respiratory infections by administering to a subject in need thereof an effective amount of a composition/adjuvant of the present invention in combination with an antigen, e.g. an antigen derived from a virus of bacterium.

Particular embodiments include treating or preventing a cancer in a subject in need thereof, comprising providing to the subject an effective amount of a cancer antigen in combination with a composition/adjuvant of the present invention. It also includes related methods of inhibiting tumor growth, reducing tumor size, and inhibiting tumor metastasis. In particular embodiments, tumor growth, tumor size, or tumor metastasis is inhibited or reduced by at least 10%, 20%, 50%, 75%, or 90% as compared to in the absence of treatment with a vaccine of the present. In particular embodiments, the subject has been diagnosed with a tumor or tumor metastasis, whereas in other embodiments, the subject is considered to be a risk of developing a tumor or tumor metastasis.

The tumor may be any type of tumor or cancer, including but not limited to solid tumors and liquid tumors. In particular embodiments, the tumor is a breast cancer, lung cancer, prostate cancer, colorectal cancer (e.g., colon carcinoma), brain cancer, esophageal cancer, stomach cancer, bladder cancer, pancreatic cancer, cervical cancer, head and neck cancer, ovarian cancer, melanoma, leukemia, myeloma, lymphoma, glioma, Non-Hodgkin's lymphoma, leukemia, multiple myeloma or multidrug resistant cancer.

In certain embodiments, the composition/vaccine is provided nasally, orally or parenterally, e.g., intravenously, subcutaneously, or intramuscularly.

In particular amounts, an effective amount of the vaccine comprises, e.g.: about 100 ug to about 500 ug (or 100 ug to about 200 ug) of antigen; about 1 ml to about 5 ml (e.g., about 1 ml) of TLR ligand; and about 1% to about 20%, about 2% to about 15%, about 2.5% to about 10%, about 5% to about 10%, or about 5% (v/v) of a cellular adhesion agent, such as carboxymethyl cellulose of a PEG. In particular embodiments, the effective amount of the vaccine comprises: 100 to 500 ug of antigen; about 1-4 ml of cationic liposome-DNA complexes; and about 5% to about 10% (v/v) of carboxymethyl cellulose. In certain embodiments, these effective amounts are present in a 1 ml vaccine. In certain embodiments, the adjuvant compositions comprise the same components in the same relative amounts but lack the antigen.

Compositions and vaccines of the present invention may be provided according to various dosing regimens. In certain embodiments, the composition or vaccine is provided once or more than once, e.g., two, three, four, five, six, seven, eight, nine, ten or more times. In particular embodiments, the composition or vaccine may be provided daily, every other day, twice a week, weekly, every other week, once a month, or once every other month.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

To test the effects of adding carboxy-methylcellulose (CMC) on the adhesion properties of liposome-TLR3/9 complexes, complexes of liposomes and DNA and TLR3/9 agonists (plasmid DNA and pIC) were labeled with a fluorescent dye, and adherence to a rat epithelial cell line was evaluated by a 3 h assay with shaking in an incubator. The effects of adding different concentrations of CMC to liposome-TLR3/9 complexes (CALNAC) was assessed by flow cytometric measurement of the percentages of epithelial cells containing liposome-TLR3/9 complexes. As best shown in FIG. 1, the addition of CMC to liposome-TLR3/9 complexes increases adhesion to epithelial cells.

Example 2

In order to assess the effects of combing TLR3 and TLR9 agonists with liposomes, spleen cells from mice were incubated with cationic liposomes alone, or liposomes+pIC or liposomes plus pDNA, or liposomes plus both pIC and pDNA. Immune stimulation (IL-12 release) was measured by ELISA assay. The combination of both TLR3 and 9 agonists generated synergistic immune activation. As best shown in FIG. 1, the combination of TLR3 and TLR9 agonists with liposomes increases potency of immune activation.

Example 3

Figure 2:
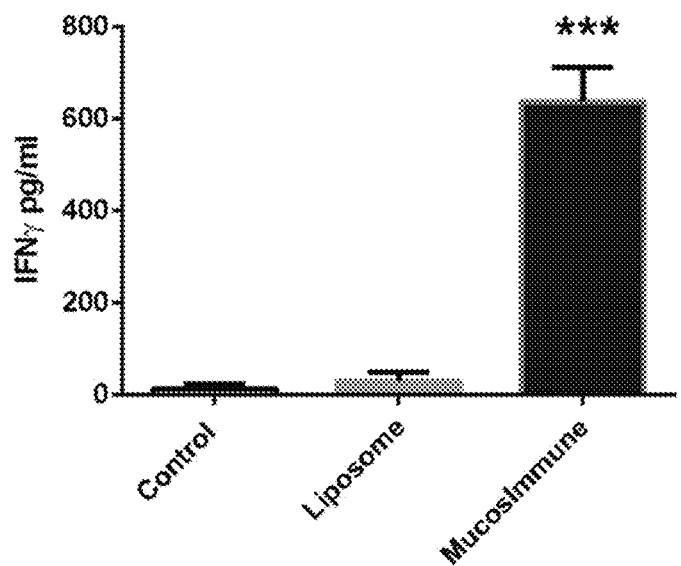
FIG. 2 shows data from a canine PBMC stimulation assay demonstrating increased immune stimulatory potency by inclusion of CMC with an immune stimulatory complex.

In order to evaluate the effect of CMC on the immune potency, canine PBMC were incubated with CLDC complexes or CLDC+10% CMC for 24 h. IFN-g release measured by ELISA as an indication of immune stimulation potency. FIG. 2 shows the immune potency comparison of complexes of cationic liposomes and pIC and pDNA alone (CLDC) or CLDC plus 10% CMC (PCT-01). Complexes of CLDC+CMC (PCT-01) were significantly more immune stimulatory than CLDC complexes.

Example 4

Figure 3:
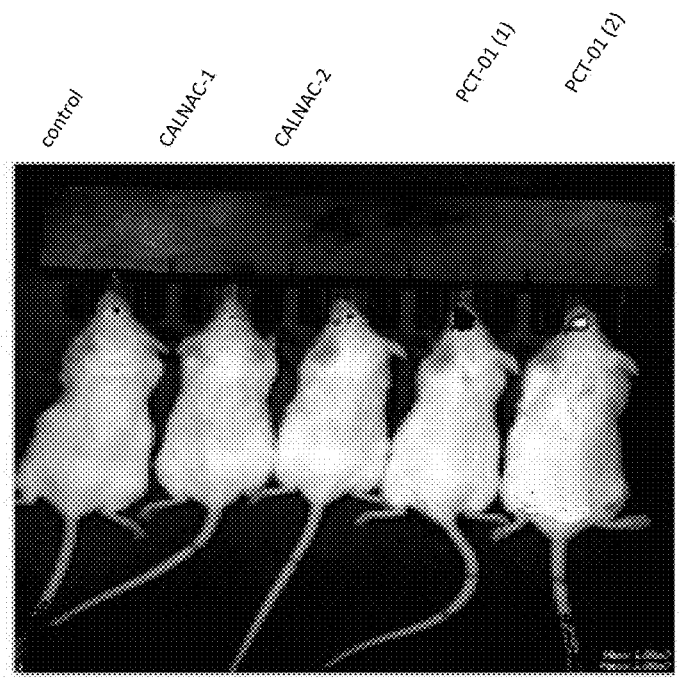
FIG. 3 shows exemplary imaging data from mice demonstrating increased in nasal cavity adhesion When animals are administered an immune stimulant (CLDC) combined with CMC (ie, PCT-01), compared to administration of CLDC alone.

To test the ability of CMC to affect adhesion to mucosal surfaces, mice were administered intranasally 50 µl CLDC or CLDC+CMC that had been labeled with a fluorescent dye to allow tracking in a live animal imager (IVIS). The amount of labeled material still present in the nostrils 60 min after administration was determined by live animal imaging. As shown in FIG. 3, compared to control animals (n=1) and animals administered CLDC (labeled CALNAC) alone (n=2), animals treated with CLDC+CMC (PCT-01, n=2) had significantly more material retained in their nostrils, indicating CMC contributes to mucosal surface adhesion.

Figure 4:
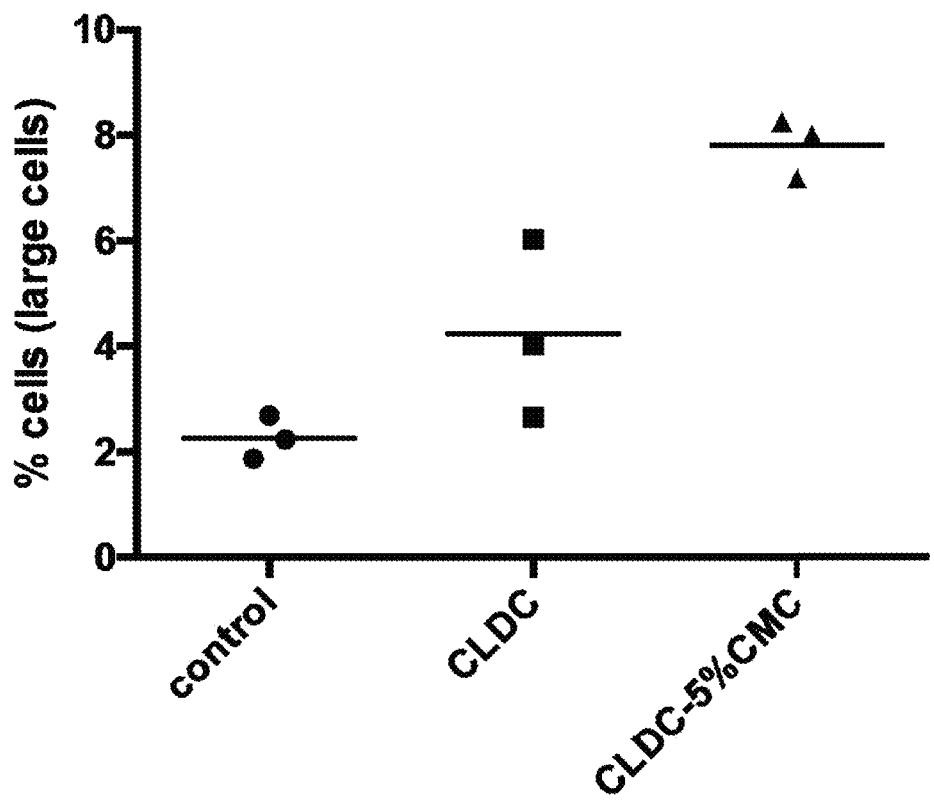
FIG. 4 shows flow cytometry data demonstrating increased immune response to PCT-01 administration in oropharynx of mice relative to CLDC alone treatment groups.
Figure 5:
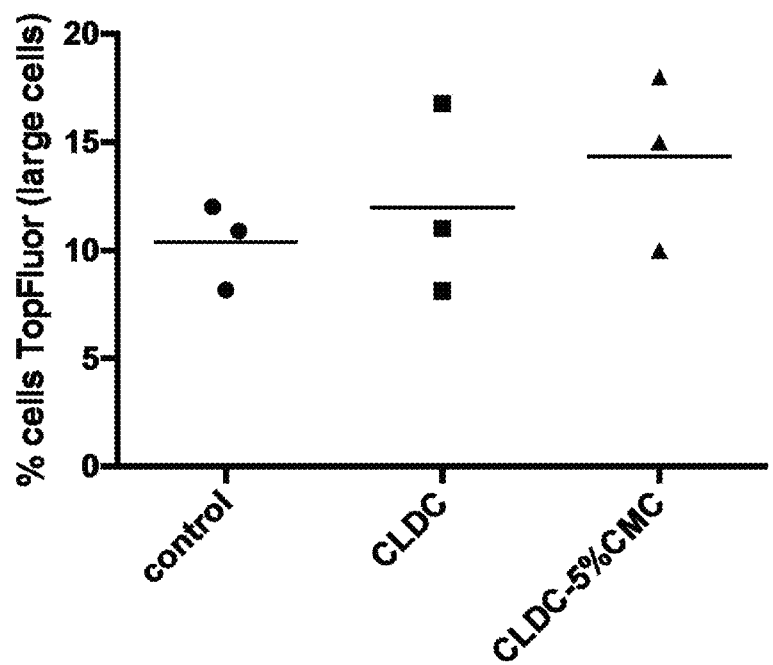
FIG. 5 shows flow cytometry data demonstrating increased immune response to PCT-01 administration in oropharynx of mice relative to CLDC alone treatment groups.

To assess the effect of CMC on the ability of CLDC to elicit immune response, mice (n=3 per group) were administered CLDC or CLDC+CMC (ie, PCT-01) orally, and 24 hours later, infiltrates of immune cells into the oropharynx was assessed by flow cytometry, using cells obtained from the oropharynx by swabs. As shown in FIG. 4, compared to control animals and animals treated with CLDC, animals treated with PCT-01 had a much stronger influx of immune cells into the oropharynx. To test the effect of nasal administration, mice (n=3 per group) were administered CLDC or CLDC+CMC (ie, PCT-01) intranasally, and 24 hours later, infiltrates of immune cells into the nasal cavity was assessed by flow cytometry, using cells obtained from the nasal cavity by nasal lavage. As shown in FIG. 5, compared to control animals and animals treated with CLDC, animals treated with PCT-01 had a much stronger influx of immune cells into the oropharynx.

Example 5

Figure 6A:
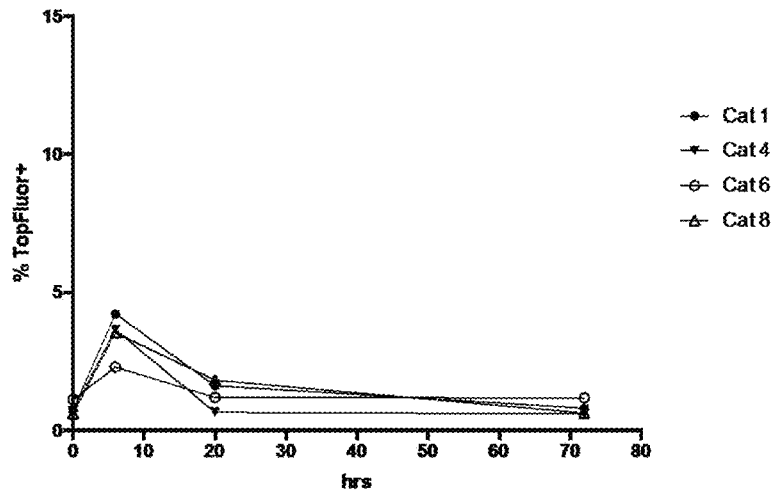
FIG. 6A shows flow cytometry data showing liposome uptake by nasal cells in cats treated intranasally with CLDC.
Figure 6B:
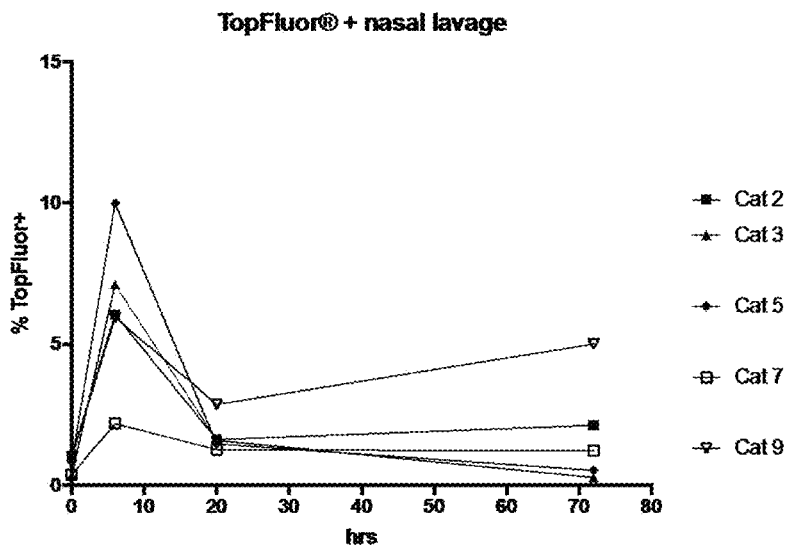
FIG. 6B shows cytometry data showing liposome uptake by nasal cells in cats treated intranasally with PCT-01.
Figure 7A:
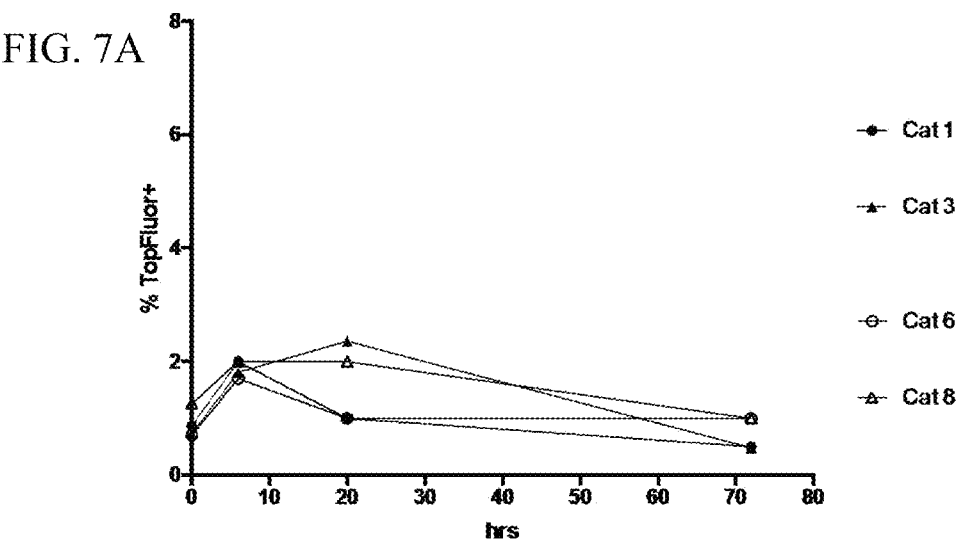
FIG. 7A shows flow cytometry data from oropharyngeal cells from cats treated with CLDC alone.
Figure 7B:
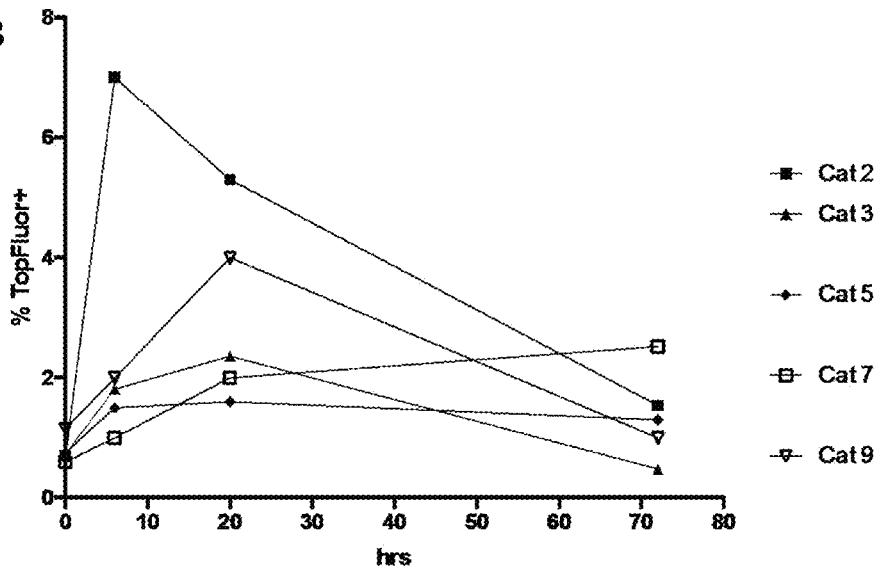
FIG. 7B shows flow cytometry data showing oropharyngeal cells from cats treated with PCT-01 (CLDC+CMC).

To assess the effect of CMC on the ability of CLDC to elicit immune response in felines, cats were treated intranasally with PCT-01 (CLDC+CMC) (n=5) and compared to cats treated with CLDC (n=4). To conduct the study, liposomes were labeled with a fluorescent dye to track their uptake by cells in the nasal and oropharyngeal mucosal. Healthy purpose-bred cats were treated intranasally with 0.3 ml labeled CLDC+CMC or labeled CLDC in each nostril. 24 hours later, nasal lavage samples were obtained and the percentage of cells that had contained labeled liposomes (TopFluor+) were compared between treatment groups, using flow cytometry. As shown in FIGS. 6A & B, nasal cells from cats treated with PCT-01 (FIG. 6A) had substantially more liposomes than from cats treated with CLDC (FIG. 6B). The study was repeated to assess liposome uptake by cells in the oropharynx. Healthy purpose-bred cats were treated orally with 1 ml labeled PCT-01 (n=5) or labeled CLDC (n=4) in each nostril. 24 h later, oropharyngeal swab samples were obtained and the percentage of cells that had contained labeled liposomes (TopFluor+) were compared between treatment groups, using flow cytometry. As shown in FIGS. 7A & B, oropharyngeal cells from cats treated with PCT-01 (FIG. 7A) had substantially more liposomes than from cats treated with CLDC (FIG. 7B).

Figure 8A:
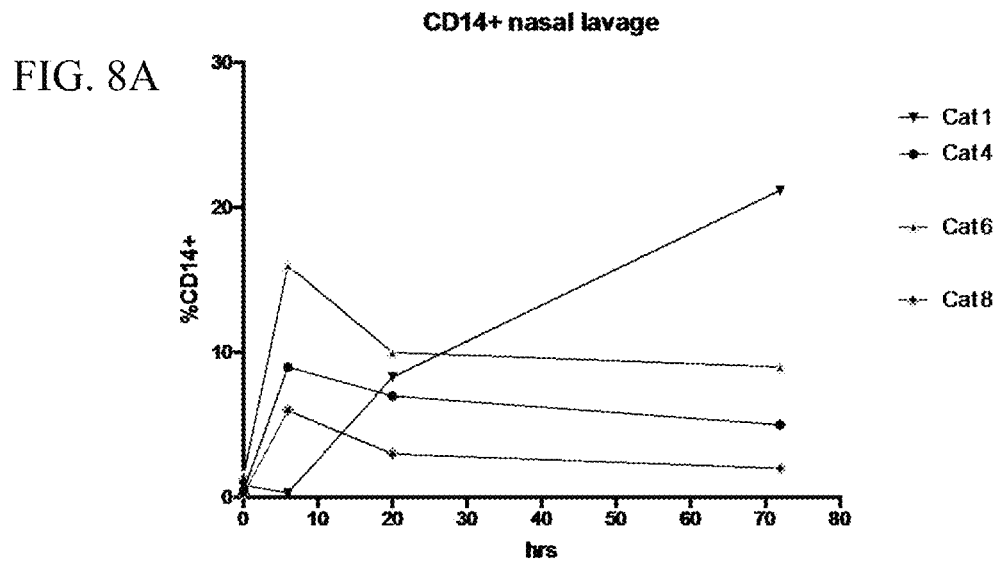
FIG. 8A shows cytometry data from nasal lavage samples from cats treated with CLDC alone.
Figure 8B:
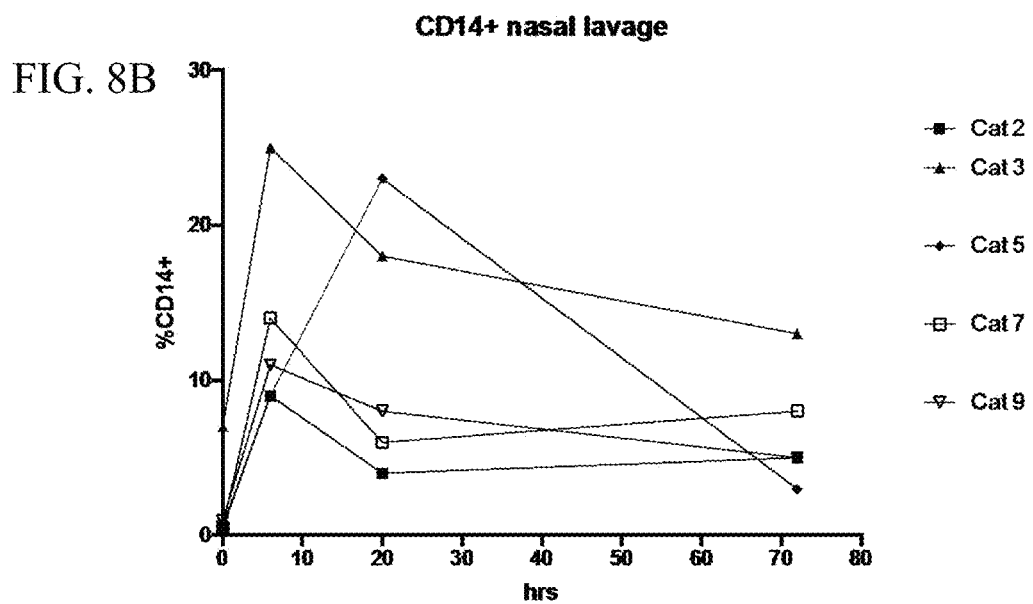
FIG. 8B shows demonstrating flow data from nasal lavage samples from cats treated with PCT-01.

FIGS. 8A & B show increase in recruitment of nasal immune cells in cats treated intranasally with PCT-01 (CLDC+CMC) (n=5) compared to cats treated with CLDC (n=4). Healthy purpose-bred cats were treated intranasally with 0.3 ml PCT-01 or CLDC in each nostril. 24 hours later, nasal lavage samples were obtained and the percentage of Cd14+ monocytes (immune cells) in the nose were compared between treatment groups, using flow cytometry. Nasal lavage samples from cats treated with PCT-01 (FIG. 8A) had substantially more CD14+ monocytes than from nasal lavage samples from cats treated with CLDC (FIG. 8B). Substantial infiltrates of monocytes were observed in both the nose and throat of the treated cats, attesting to local immune stimulation by PCT-01.

Example 6

Figure 9:
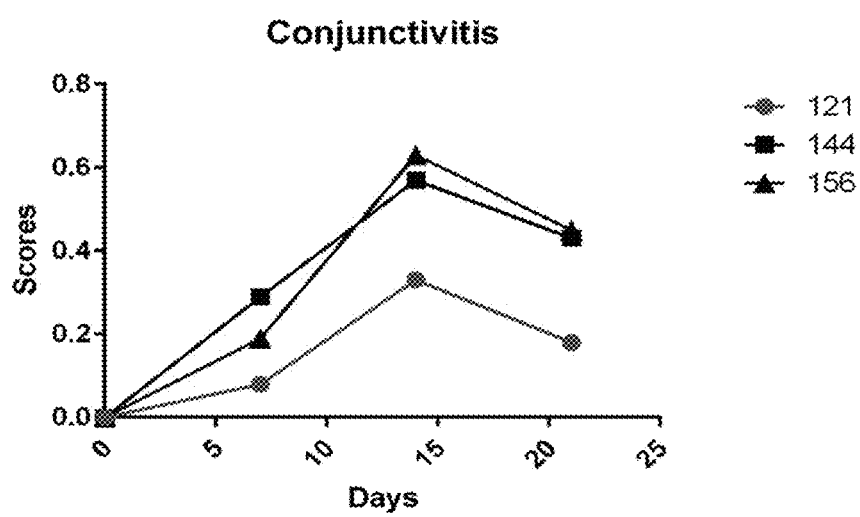
FIG. 9 shows data demonstrating reduced clinical signs of ocular disease in cats challenged with FHV-1 and pre-treated 24 h prior to challenge with PCT-01.
Figure 10:
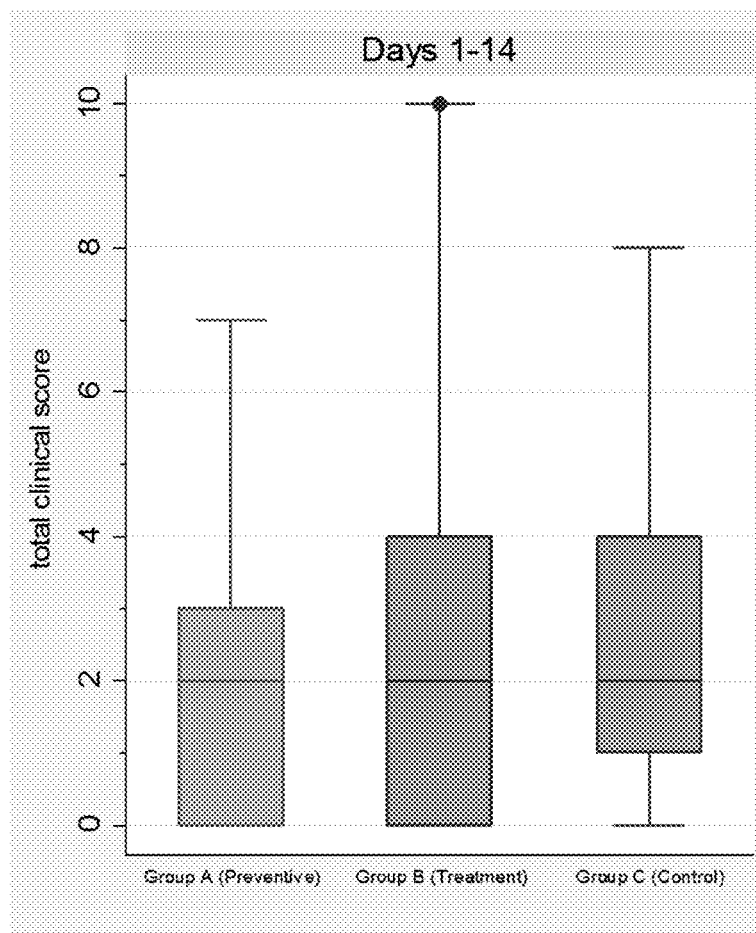
FIG. 10 shows clinical illness in cats pre-treated with PCT-01 24 h prior to FHV-1 challenge.
Figure 11:
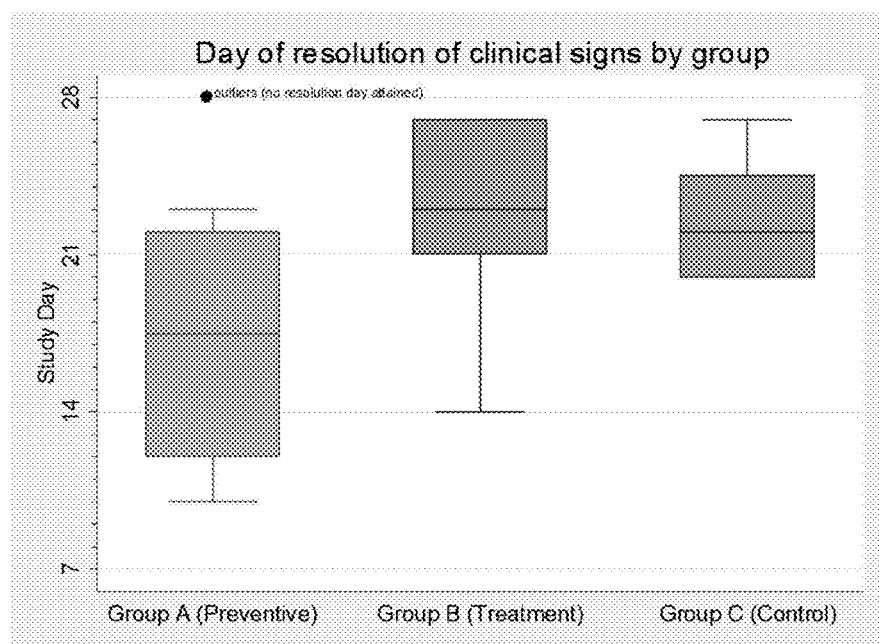
FIG. 11 shows clinical data indicating time to resolution of clinical signs significantly shortened in cats pre-treated with PCT-01.

To test the ability of PCT-01 to affect clinical signs of ocular disease, a challenge study with feline herpesvirus type 1 (FHV-1) was conducted in purpose-bred cats. Three groups of cats (n=7 per group) including untreated control cats (group 156), cats pre-treated with PCT-01 24 h prior to challenge (group 121) and cats treated with PCT-01 when symptoms first developed (group 144), were monitored for clinical signs of infection (ocular signs, total clinical signs, body temp) and viral shedding by qRT-PCR for 28 days after the viral challenge was administered. As shown in FIG. 9, cats pre-treated with PCT-01 before challenge had a significant reduction in clinical ocular signs (squinting, ocular discharge) compared to control animals. As best seen in FIG. 10, total clinical scores in cats challenged with FHV-1 (FIG. 9) and pre-treated 24 h before challenge with PCT-01 were significantly lessened compared to control cats and cats treated after clinical signs developed. Furthermore, as seen in FIG. 11, cats challenged with FHV-1 and treated 24 h before onset of clinical signs experienced a significant reduction in the duration of clinical signs compared to control animals or animals treated once signs developed.

Figure 12:
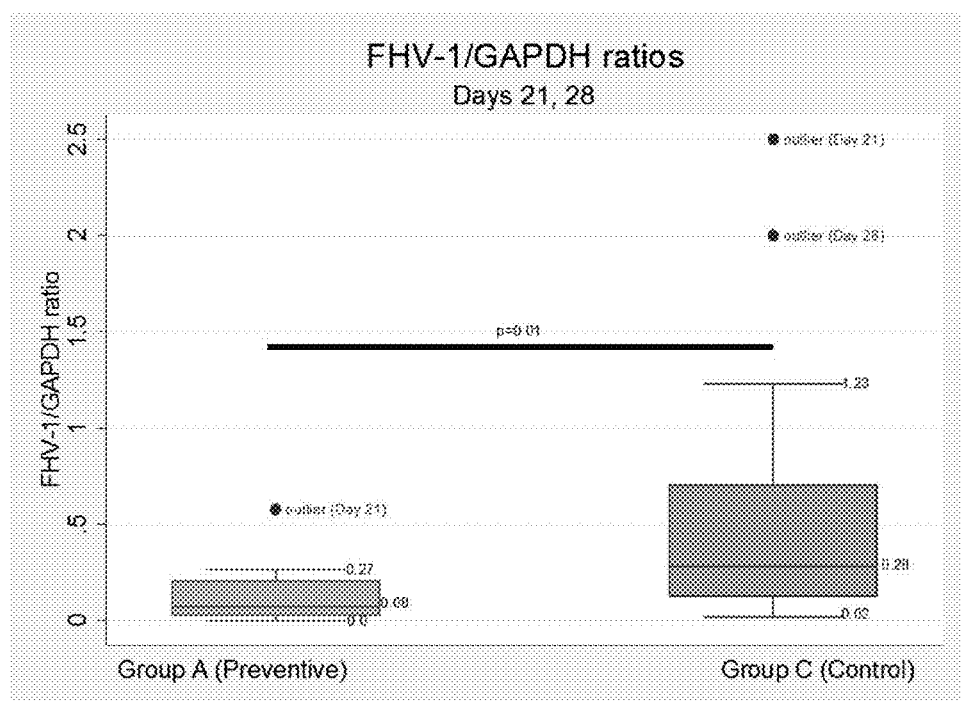
FIG. 12 shows qRT-PCR data indicating PCT-01 treatment significantly decreased viral shedding in cats challenged with FHV-1.

FIG. 12 shows Pre-treatment with PCT-01 significantly decreases viral shedding in cats challenged with FHV-1. Cats were pre-treated 24 h prior to FHV-1 challenge with PCT-01, and viral shedding from oropharyngeal swabs (as assessed by qRT-PCR) was compared to viral shedding by untreated control animals. As shown in FIG. 12, pre-treated with PCT-01 resulted in a significant decrease in viral shedding compared to untreated animals.

Example 7

To assess the uptake of labeled PCT-01 by nasal and oropharyngeal cells in dogs, labeled PCT-01 were administered intranasally and orally to a healthy adult dog. 6 h and 20 h later, nasal lavage and throat swab samples were obtained, and the percent of cells containing labeled liposomes determined. As shown in FIGS. 13A & B, These studies found a substantial uptake of liposomes by nasal (FIG. 13A) and oropharyngeal (FIG. 13B) cells at 6 h and 20 h after administration.

Figure 14A:
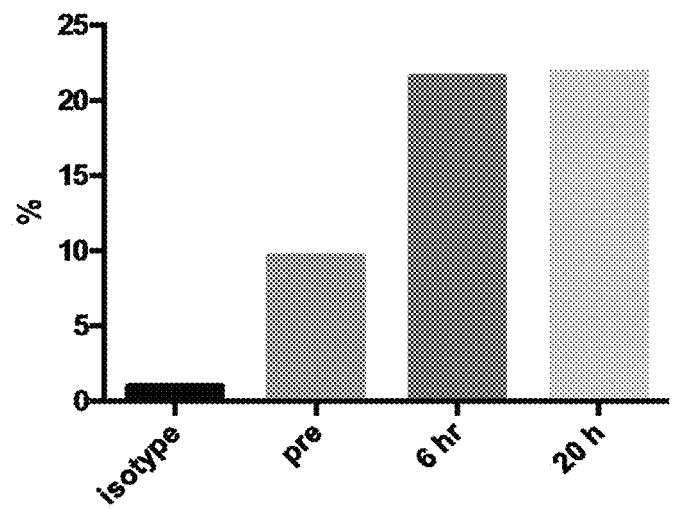
FIG. 14A shows data quantifying the increase in immune cell infiltrates in the nose of dogs following PCT-01 treatment.
Figure 14B:
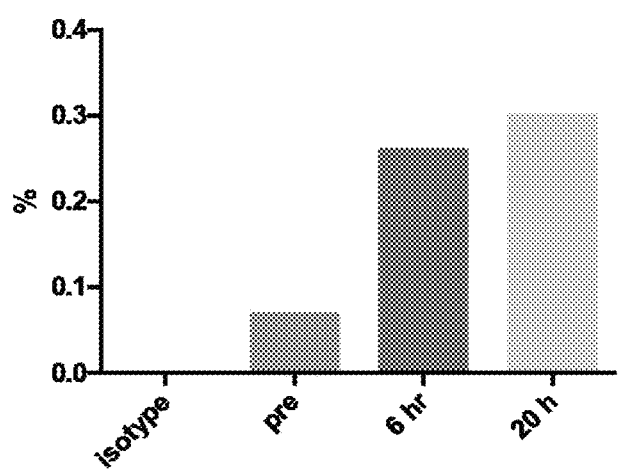
FIG. 14B shows data quantifying the increase in immune cell infiltrates in the throat of dogs following PCT-01 treatment.
Figure 15A:
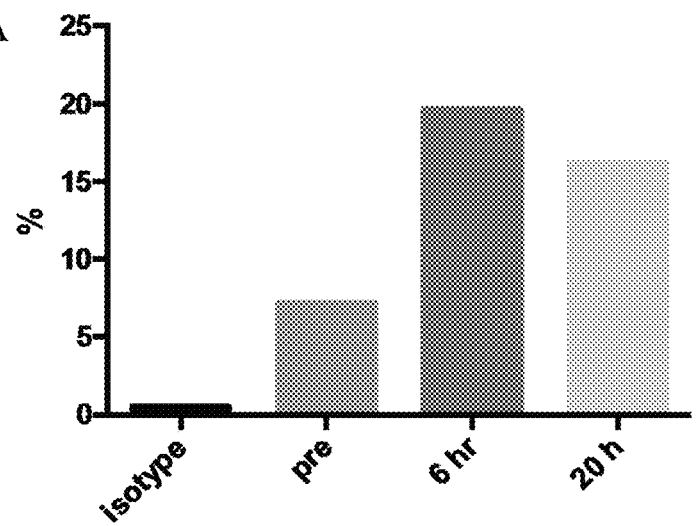
FIG. 15A shows data quantifying stimulation of CD4 T cell infiltrates into canine nasal lavage cells following PCT-01 treatment.
Figure 15B:
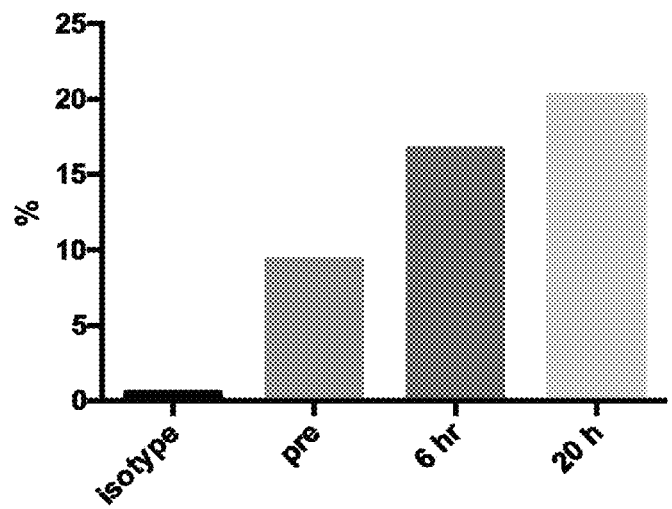
FIG. 15B shows data quantifying stimulation of CD4 T cell infiltrates into canine throat cells following PCT-01 treatment.

To assess the stimulation of immune cell infiltrates into nose and throat of dogs, PCT-01 was administered intranasally (0.5 ml per nostril) and orally (2 ml) in a healthy adult dog. The effects on immune cell infiltrates in the nose and throat was determined 6 h and 20 h later. As shown in FIGS. 14A & B, substantial infiltrates of neutrophils and monocytes were observed in both the nose (FIG. 14A) and throat (FIG. 14B) of the treated dog, attesting to local immune stimulation by PCT-01. FIGS. 15A & B show stimulatory effect in the nose and mouth, as measured CD4 T cell infiltrates.

Figure 33:
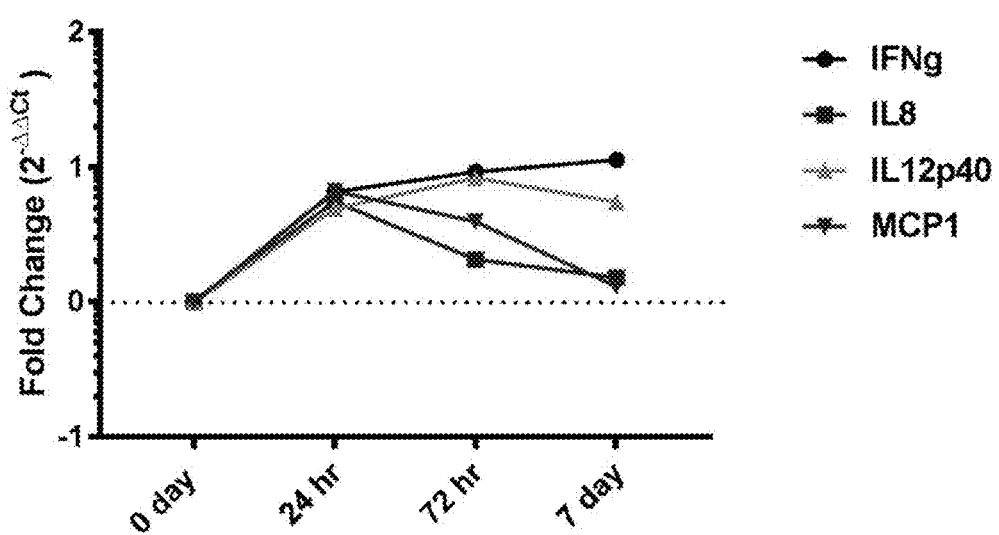
FIG. 33 shows in vivo induction of mucosal immune responses in the oropharynx of dogs treated orally with PCT-01.

Expression of cytokine genes in the oropharynx of dogs treated with PCT-01 was assessed at 3 time points (24 h, 72 h, 7 days) following treatment in healthy Beagle dogs (n=5), using qRT-PCR and primers designed for amplification of canine cytokine genes. As seen in FIG. 33, induction of cytokine expression was observed at 24 h, and persisted for at least 7 days in the treated dogs, consistent with the activation of local, mucosal immune responses by PCT-01.

FIGS. 16A & B show increased immune potency from combined TLR3 and TLR9 agonists. Spleen cells from mice were placed in culture in triplicate wells, and then incubated with the noted components for 24 hours to assess induction of immune activation (reflected by IL-12 secretion). While liposomes complexed with either polyIC or with plasmid DNA induced immune activation (IL-12 production), liposomes complexed with both pIC and pDNA together in the same complexes stimulated significantly greater immune activation.

Example 8

Figure 17A:
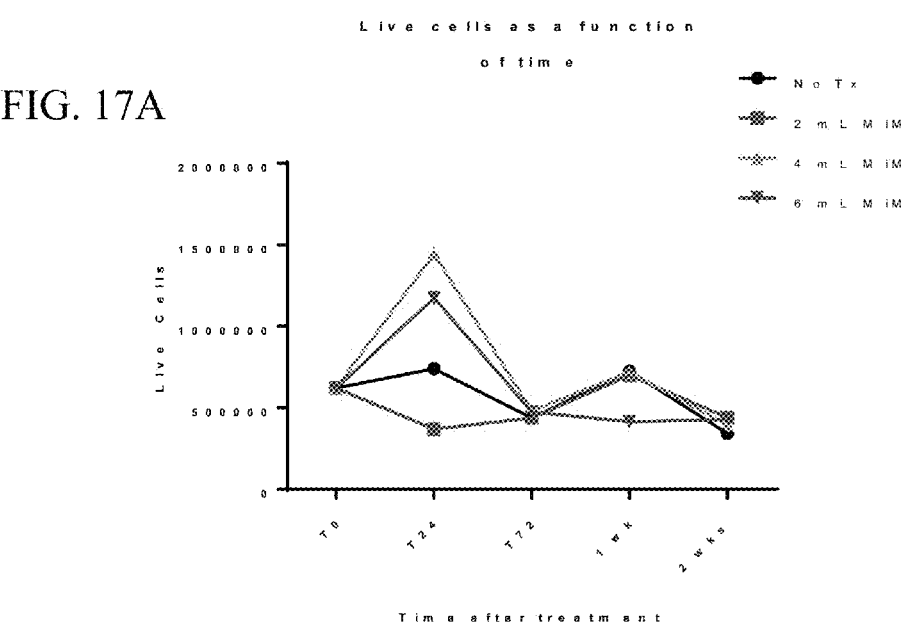
FIG. 17A shows changes in nasopharyngeal cell counts from cattle over time following a single intranasal PCT-01 administration (variable doses) compared to no treatment.
Figure 17B:
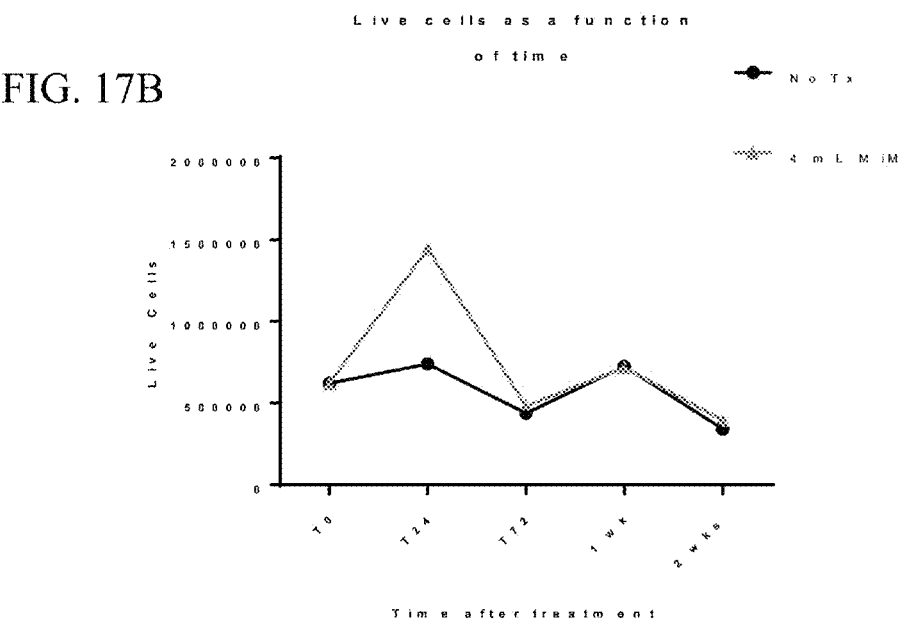
FIG. 17B shows changes in nasopharyngeal cell counts from cattle over time following a single intranasal PCT-01 administration compared to no treatment.

To assess the ability of PCT-01 to elicit a bovine immune response, cattle (n=5 per group) were treated by intra-nasal administration of 3 different doses of PCT-01 (2 ml, 4 ml, or 6 ml per animal, divided in two equal doses per nostril) using a nasal cannula. One additional untreated group served as a control (no Tx). Prior to the initial dose, and then at 24 hours, 72 hours, 1 week and 2 weeks post administration, swabs of the throat were obtained from each animal, and the cells were removed from the swab by swirling and total cell counts obtained. As shown in FIGS. 17A & B, administration of PCT-01 at the 2 highest doses (4 ml and 6 ml) elicited a significant increase in immune cell infiltration into the nasopharynx, which peaked at 24 h and then declined to normal levels by 72 h after administration.

Figure 18A:
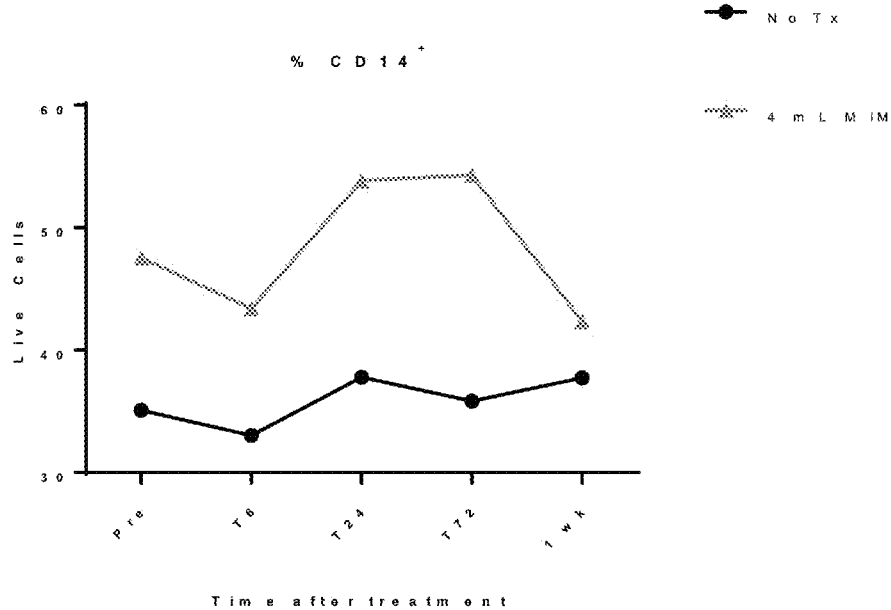
FIG. 18A shows data indicating the effects of intranasal PCT-01 administration on monocyte recruitment in cells from bovine nasopharyngeal swab specimens.
Figure 18B:
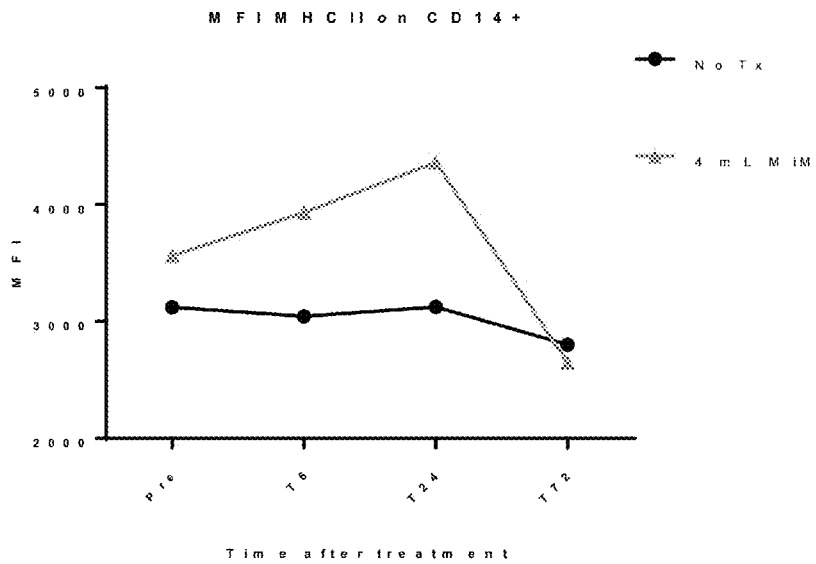
FIG. 18B shows data indicating the effects of intranasal PCT-01 administration on immune activation in cells from bovine nasopharyngeal swab specimens.

To test the effects of PCT-01 administration on monocyte recruitment and immune activation to the oropharynx in bovine, cattle (n=5 per group) were treated with intranasal administration 4 ml PCT-01 (MiM) (2 ml per nostril) (or treated with saline only, no Tx) and infiltrates of monocytes (CD14+ cells) in the nasopharynx were assessed by throat swabs and flow cytometric analysis. In addition, the upregulation of MHCII expression (measure of immune activation) was also assessed on the CD14+ monocytes by flow cytometry. As shown in FIGS. 18A & B administration of PCT-01 elicited a sustained increase in the percentage of monocytes in the nasopharynx (FIG. 18A) compared to untreated animals, and the monocytes were also activated, as reflected by upregulation of MHCII expression (FIG. 18B).

Figure 19:
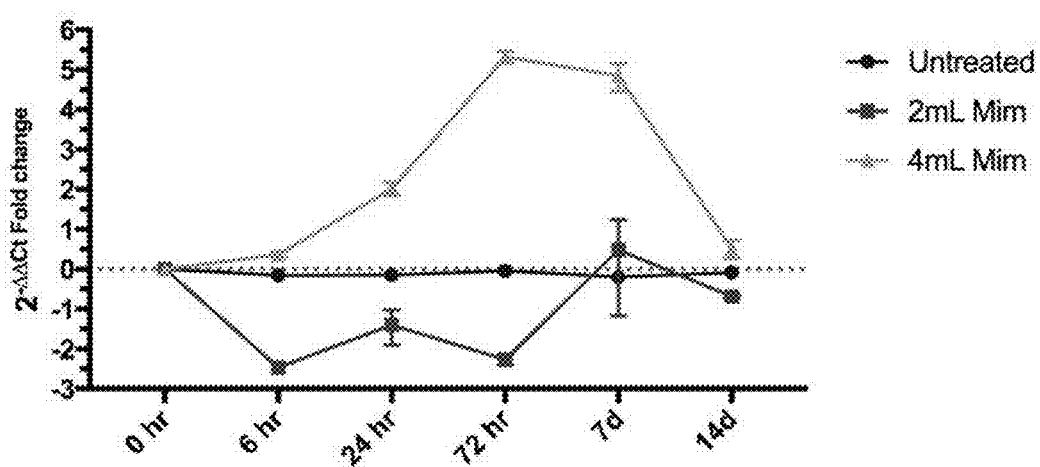
FIG. 19 shows qRT-PCR data indicating intra-nasal administration of PCT-01 stimulates production of the cytokine IL-8 by cells in the nasopharynx of cattle.
Figure 20:
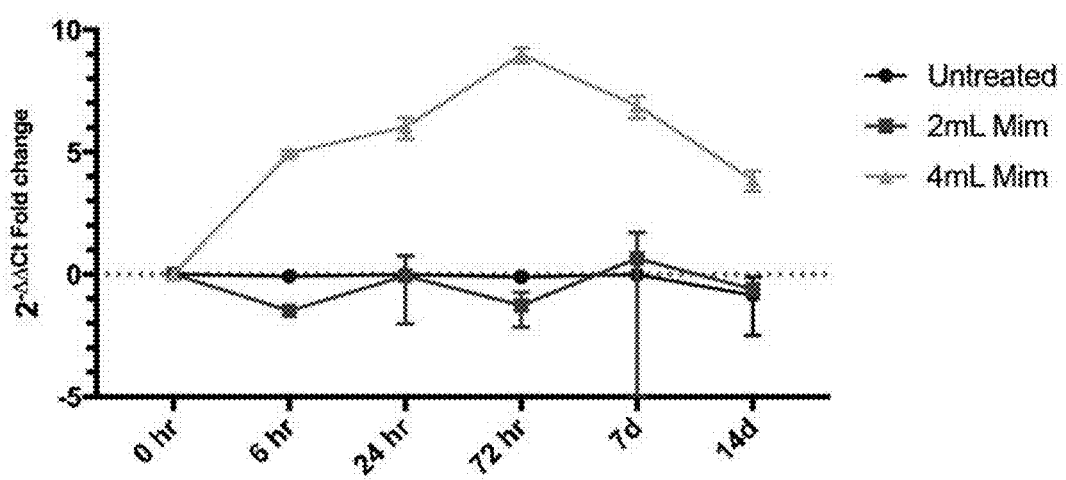
FIG. 20 shows qRT-PCR data indicating intra-nasal administration of PCT-01 stimulates production of the cytokine MCP-1 by cells in the nasopharynx of cattle.
Figure 21:
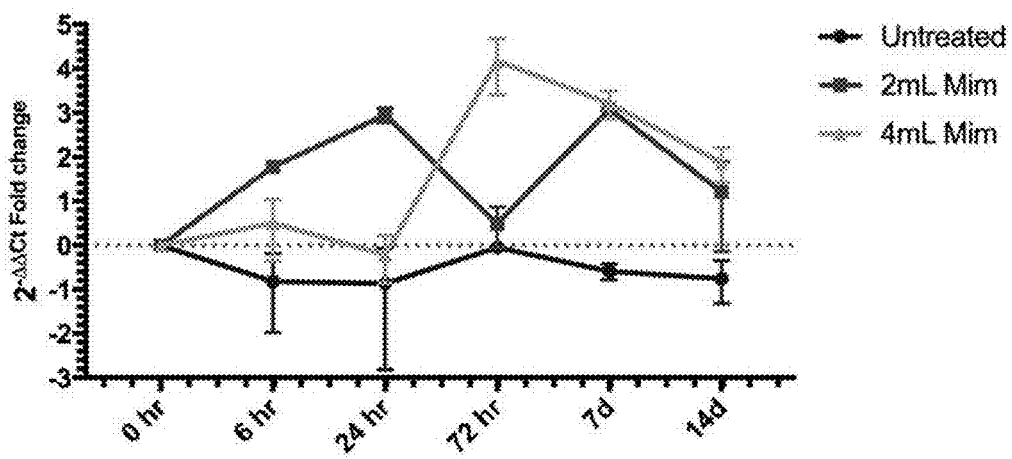
FIG. 21 shows qRT-PCR data indicating intra-nasal administration of PCT-01 stimulates production of the cytokine IFN-g by cells in the nasopharynx of cattle.

To test the ability of PCT-01 to stimulate bovine cytokine production, cattle (n=5 per group) were administered PCT-01 intranasally (2 ml or 4 ml) and cells obtained by nasopharyngeal swabbing were evaluated using qRT-PCR for cytokine expression. FIG. 19 shows administration of 4 ml PCT-01 resulted in sustained expression of mRNA for cytokine IL-8 in nasopharyngeal cells for up to 14 days. FIG. 20 shows that administration of 4 ml PCT-01 resulted in sustained expression of mRNA for cytokine MCP-1 in nasopharyngeal cells for up to 14 days. FIG. 21 shows that administration of 4 ml PCT-01 resulted in sustained expression of mRNA for cytokine IFN-g in nasopharyngeal cells for up to 14 days.

Example 9

Figure 16:
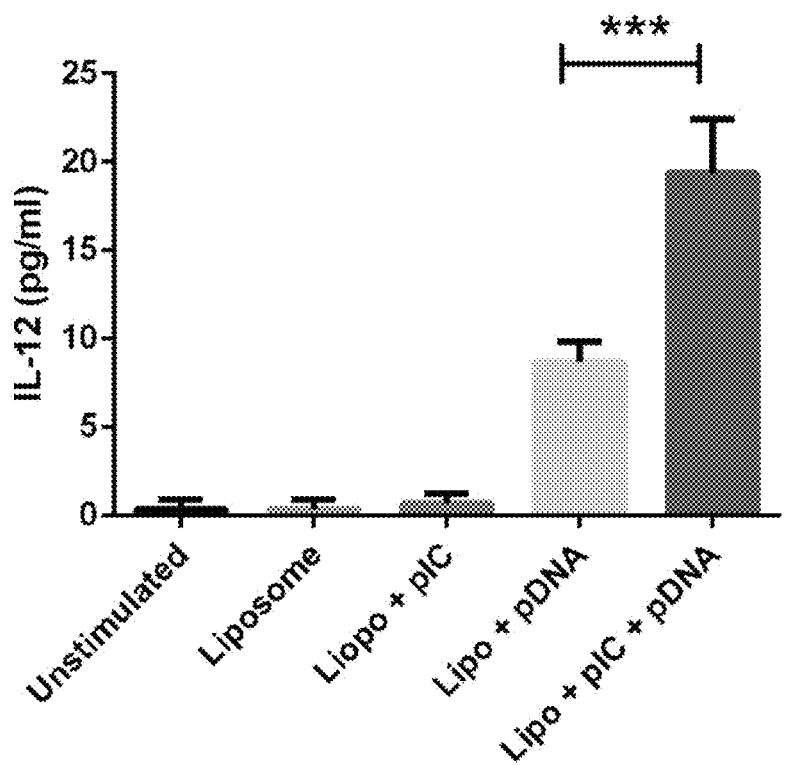
FIG. 16 shows IL-12 expression data indicating increased in vitro immune potency from combined TLR3 and TLR9 agonists, as present in PCT-01.
Figure 22A:
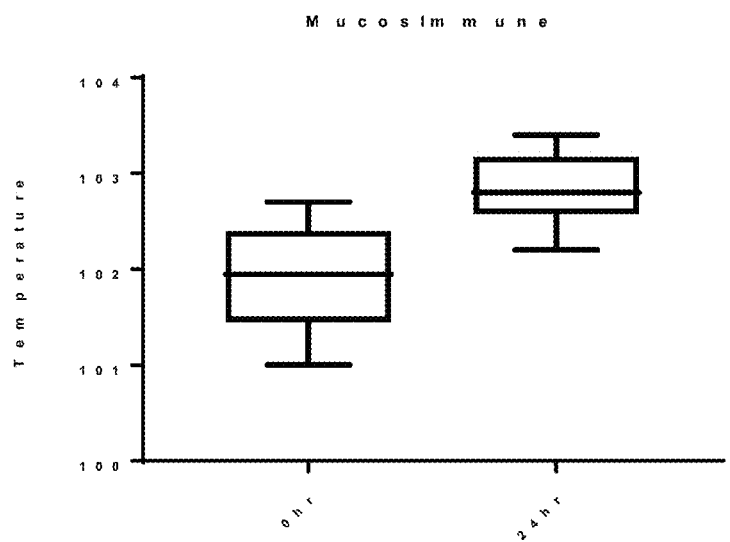
FIG. 22A shows body temperature data in cattle following administration of PCT-01.
Figure 22B:
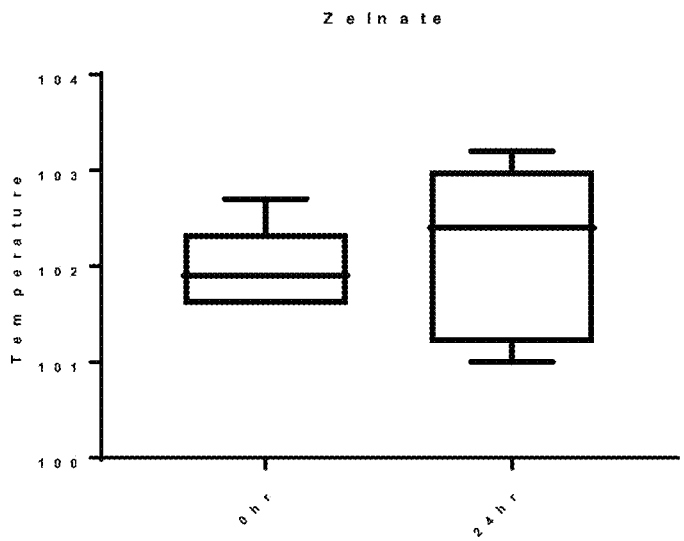
FIG. 22B shows body temperature data in cattle following administration of Zelnate.
Figure 23:
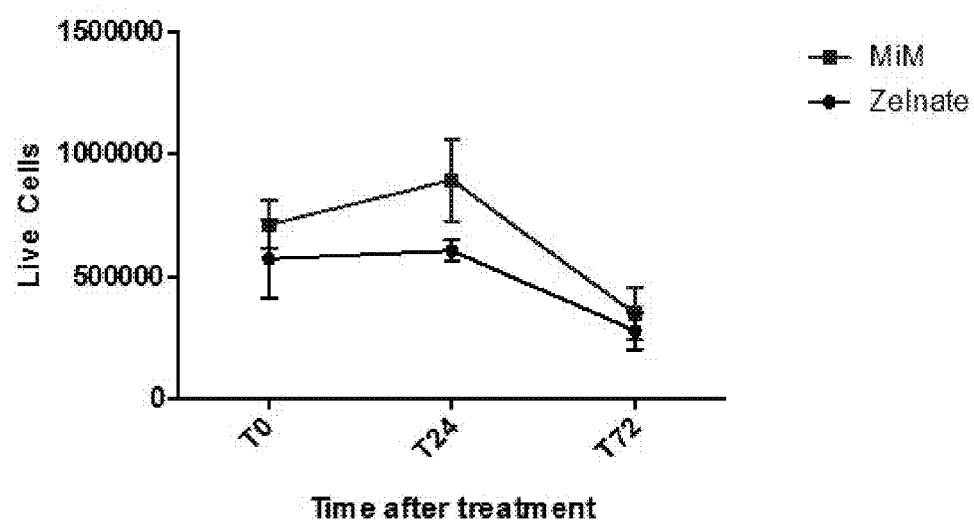
FIG. 23 shows data comparing immune activation of monocytes, as measured by total cell count, in the nasopharynx of cattle following intranasal administration of PCT-01 or IM administration of Zelnate.
Figure 24:
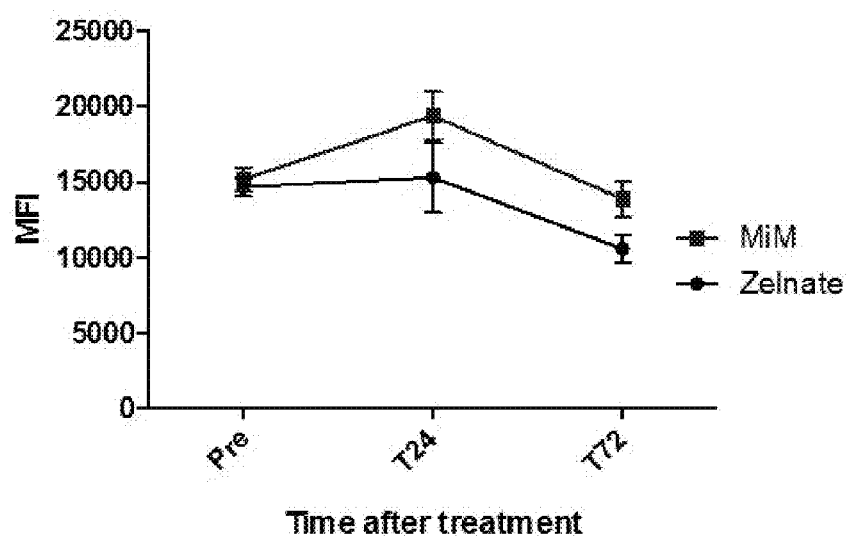
FIG. 24 shows data comparing immune activation of monocytes, as measured by upregulation of MHCII, in the nasopharynx of cattle following intranasal administration of PCT-01 or IM administration of Zelnate.
Figure 25:
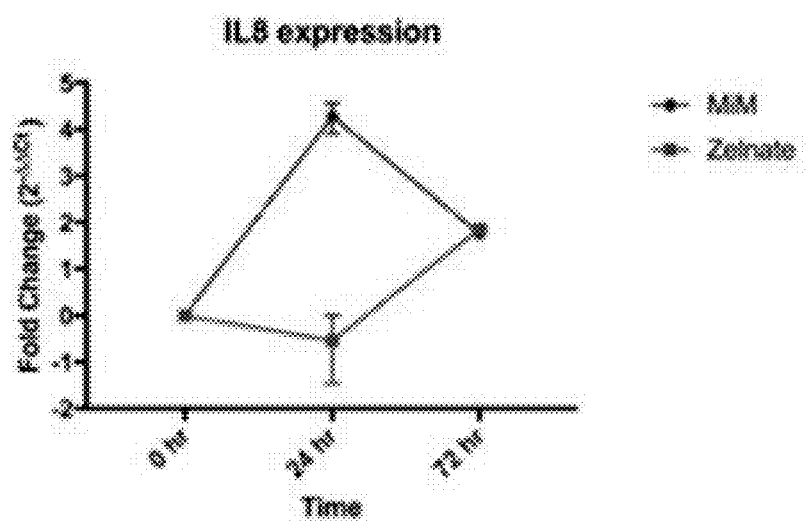
FIG. 25 shows qRT-PCR data from cattle indicating increased IL-8 expression by PCT-01 treatment, compared to Zelnate treatment.
Figure 26:
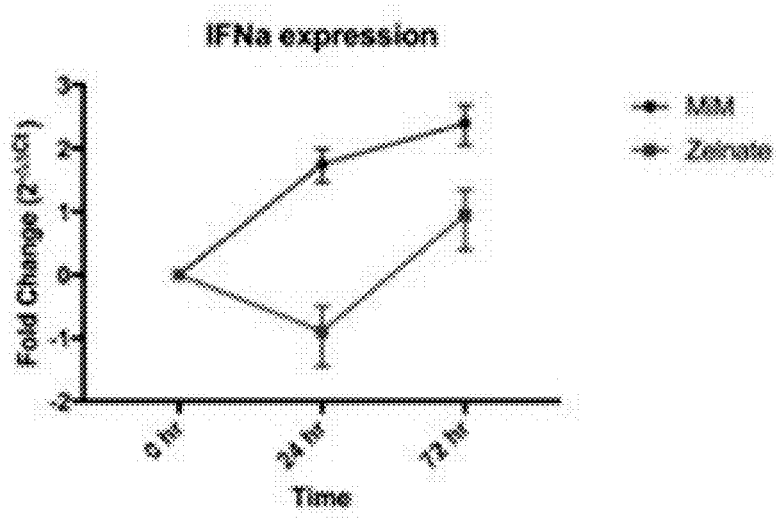
FIG. 26 shows qRT-PCR data from cattle indicating increased INF-a expression by PCT-01 treatment, compared to Zelnate treatment.
Figure 27:
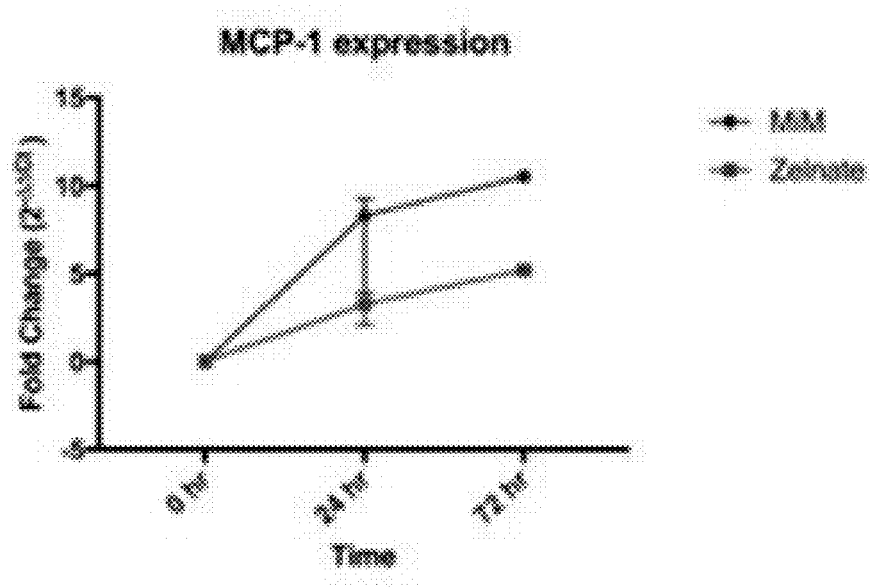
FIG. 27 shows qRT-PCR data from cattle indicating increased MCP-1 expression by PCT-01 treatment, compared to Zelnate treatment.

To assess the ability of PCT-01 to induce immune activity relative to other immune stimulants known in the art, two groups of cattle (n=5) were administered either PCT-01 (4 ml/2 mL per nostril) or Zelnate (I.M. per manufacturer guidance) and the immune response was measured prior to treatment, 24 hours post-treatment, and 72 hours post-treatment. FIGS. 22A & B show that after 24 hours, PCT-01 treatment (FIG. 22A) yielded a larger increase in body temperature than Zelnate treatment (FIG. 22B). FIG. 23 shows data from flow cytometry analysis of nasopharyngeal swabs indicating greater upregulation of MHCII expression by monocytes (CD14+) in PCT-01 treated groups than in Zelnate treated groups. FIG. 24 shows data from qRT-PCR studies indicating IL-8 expression was upregulated to a much greater degree by PCT-01 administration compared to Zelnate administration. Furthermore, PCT-01 administration produced a much more rapid upregulation of IL-8 than did Zelnate administration. qRT-PCR was also used to assess INF-a expression following PCT-01 and Zelnate administration. FIG. 16 shows INF-a expression was upregulated to a much greater degree by PCT-01 administration compared to Zelnate administration. Furthermore, PCT-01 administration produced a much more rapid upregulation of INF-$\alpha$ than did Zelnate administration. qRT-PCR studies were also performed to assess MCP-1 expression. FIG. 27 shows that PCT-01 produced a more robust induction of MCP-1 than administration of Zelnate. Taken together, these data indicate that relative to Zelnate, PCT-01 produces significantly greater immune stimulatory effect.

Example 10

Figure 28:
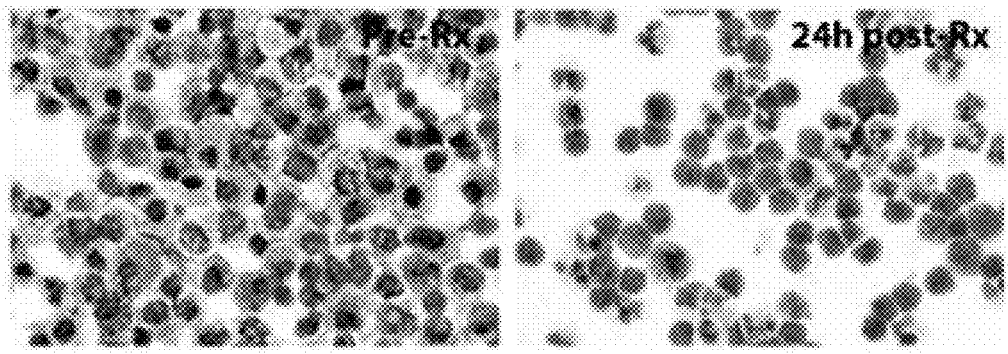
FIG. 28 shows exemplary images demonstrating increased infiltration of lymphocytes in milk samples following intra-mammary infusion of PCT-01 in dairy cattle.

In order to assess the immunological impact of PCT-01 treatment in dairy cattle, dairy cows (n=5) were infused in one quarter of the mammary gland using 1 ml PCT-01 diluted in 9 mls PBS. Pre-treatment lavage samples were obtained from the quarter 7 d before infusion (pre-Rx) and then at 24 h, 72 h, and 7 days after PCT-01 infusion. As shown in FIG. 28, milk samples were evaluated cytologically for the cellular response to PCT-01 infusion, and demonstrated an influx of mononuclear cells (T cells) into the infused mammary gland quarter. These results are indicative of local induction of mammary gland immunity by PCT-01.

Example 11

Figure 29:
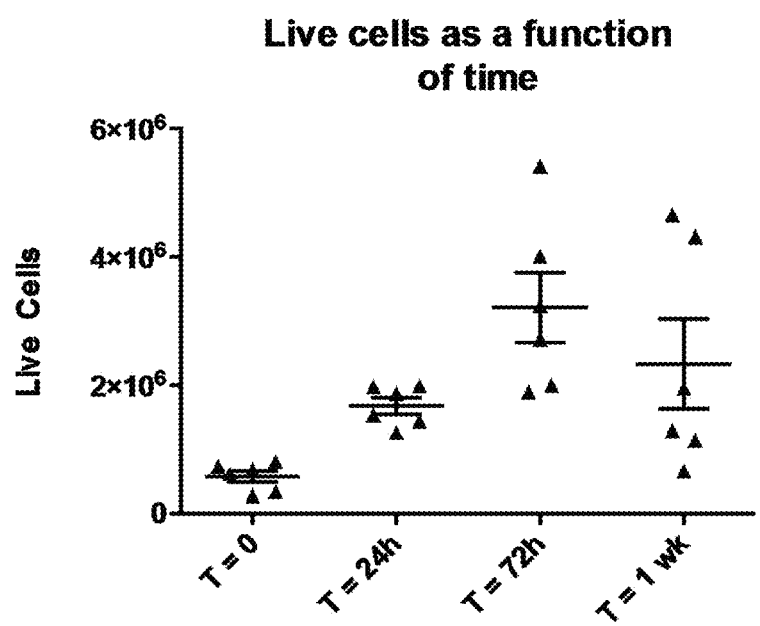
FIG. 29 shows cell count data demonstrating the cellular responses in the nasopharynx of goats following intra-nasal administration of PCT-01.

In order to assess the ability of PCT-01 to exert immunostimulatory effects in goats, nasopharyngeal swabs were obtained from healthy adult goats (n=6) before PCT-01 administration and at 24 h, 72 h, and 7 days after treatment. As shown in FIG. 29, cell counts were determined from swab samples, and were found to be significantly increased at 72 h and 7 days after treatment.

Figure 30A:
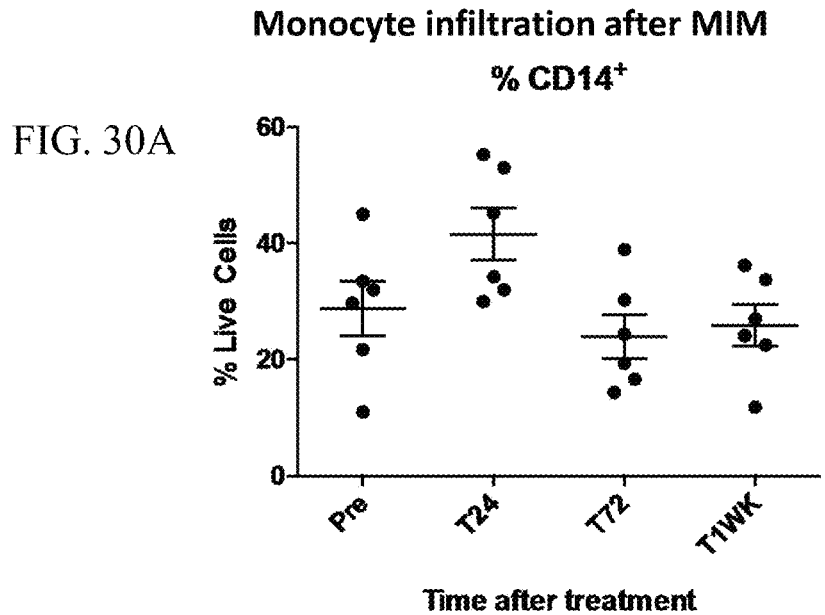
FIG. 30A shows monocyte responses, as measured by cell count, following PCT-01 intra-nasal delivery in goats.
Figure 30B:
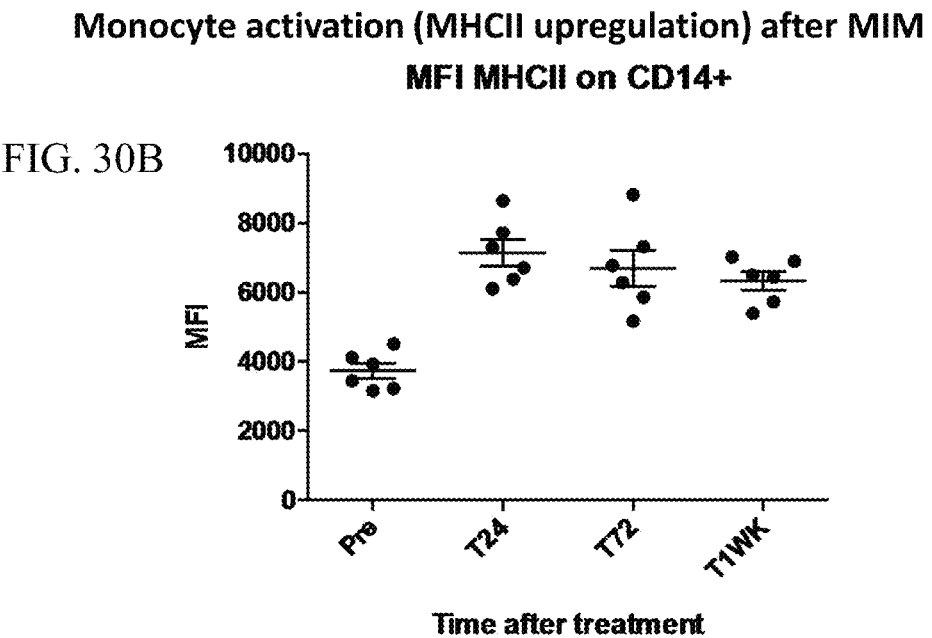
FIG. 30B shows cellular activation, as measured by MHCII upregulation, following PCT-01 intra-nasal delivery in goats.
Figure 31:
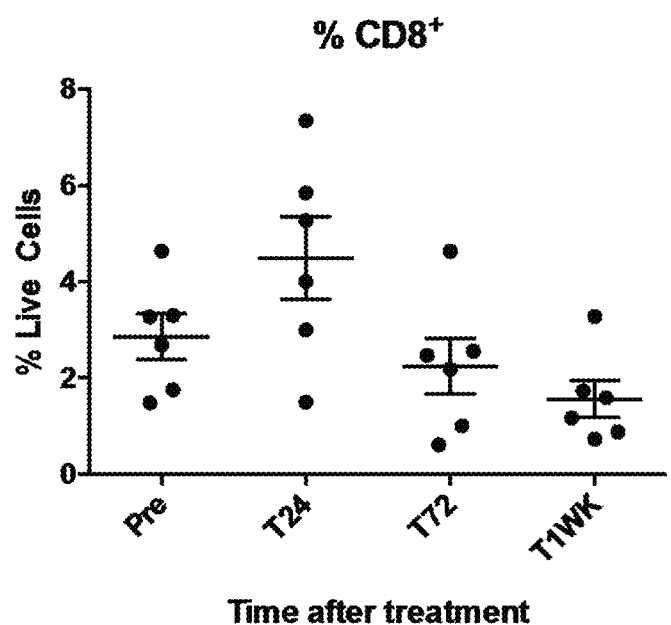
FIG. 31 shows cell count data demonstrating recruitment of CD8 T cells into nasopharynx of goats by PCT-01 intranasal administration.

To assess the effect of PCT-01 on monocyte response and cellular activation, monocyte infiltration and MHCII upregulation were assessed. As shown in FIG. 30A, the percentages of CD14+ monocytes were determined from nasopharyngeal swabs samples, and were found to be significantly increased 24 h after treatment. As shown in FIG. 30B, monocytes were found to be significantly activated (higher MHCII expression) at all post-treatment time points evaluated, indicative of sustained immune activation. Furthermore, as shown in FIG. 31, CD8 T cells were found to be significantly increased in nasopharynx swabs from goats following treatment.

Figure 32:
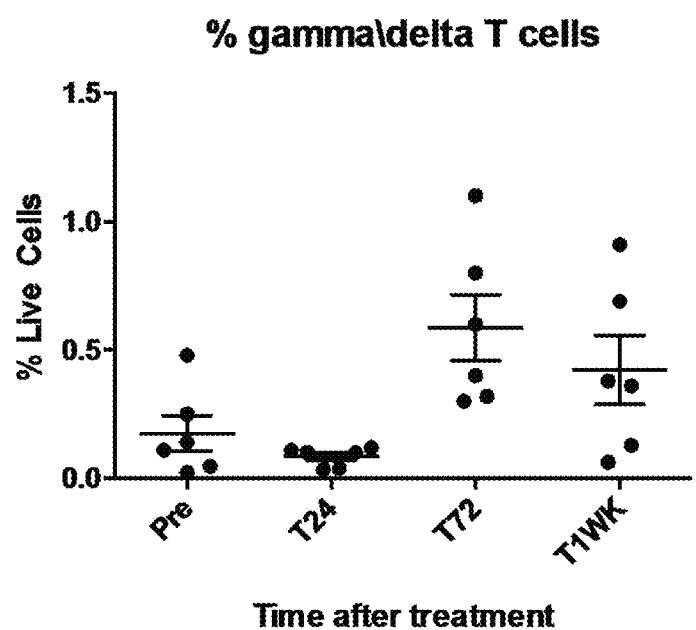
FIG. 32 shows in vitro expansion of γδ-T cells in goat PBMC cultures following PCT-01 stimulation.

As shown in FIG. 32, PCT-01 administration results in an increased percentage of $\gamma\delta$-T cells in goat cultured PBMC cells. Blood leukocytes from healthy goats were placed in triplicate wells of 96-well plates in 100 ul complete medium, and the added amounts of PCT-01 were added to the wells, and the cultures were incubated for 48 h, at which point the cells were collected and immunostained for assessment of cellular responses, using flow cytometry. The results indicated that PCT-01 induced an increase in the percentages of $\gamma\delta$-T cells in cultured goat leukocytes, compared to control cells not administered an immune stimulant.

All of the U.S. patents, U.S. patent application publications, U.S. patent applications, foreign patents, foreign patent applications and non-patent publications referred to in this specification and/or listed in any Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. An immunogenic composition comprising:
   (a) cationic liposomes, wherein the cationic liposomes comprise a mixture of cationic lipids and non-charged lipids;
   (b) a mixture of toll like receptor 3 (TLR3) and toll like receptor 9 (TLR9) ligands;
   (c) a cellular adhesion agent; and
   (d) wherein the mixture of TLR3 and TLR9 ligands comprises non-coding plasmid DNA and polyI:C in a ratio of about 1:1 (by weight).

2. The composition of claim 1, wherein the cationic liposomes comprise DOTAP and cholesterol in a 1:1 molar ratio.

3. The composition of claim 1, wherein the non-coding plasmid DNA comprises a polynucleotide represented by SEQ ID NO: 1.

4. The composition of claim 1, wherein the cellular adhesion agent is a low- to mid-weight viscosity carboxymethylcellulose.

5. The composition of claim 4, wherein the low weight viscosity carboxymethylcellulose is present at about 1% to 20% (v/v).

6. The composition of claim 1, wherein the composition comprises about 100 ug of the TLR3 and TLR9 ligands per 1 ml of a 10 mM cationic liposomes concentration.

7. The composition of claim 1, further comprising an antigen, and wherein the antigen is a viral, bacterial or tumor antigen.

8. The composition of claim 1, wherein the polyI:C comprises low molecular weight (LMW) polyI:C.

9. The composition of claim 8, wherein the LMW polyI:C is about 0.2 kb to about 1.0 kb.

10. A method for inducing an immune response to an antigen in a subject, comprising administering to the subject a composition comprising the composition of claim 1 and an antigen.

11. The method of claim 10, wherein the composition is provided to the subject orally, intranasally, intravaginally, intrauterine, by intramammary injection, subcutaneously, intradermally, intravenously, by aerosol delivery, or parenterally.

12. The method of claim 10, wherein the subject is livestock or a pet.

13. The method of claim 10, wherein the subject is selected from the group consisting of: a horse, a dog, a cat, a cow, a sheep, a pig, a goat, a chicken, and a fish.

14. The method of claim 12, wherein the composition is provided to the subject prior to and/or during boarding the subject at a facility.

15. The method of claim 10, wherein the composition is provided to the subject from 24 hours prior to exposure to a pathogen or within 24 hours to a week or more after exposure to the pathogen or a combination of administration of the composition to the subject.

16. The method of claim 10, wherein administration of the composition comprises administering to at least one of the reproductive tract, the gastrointestinal tract, the mammary gland, gills, air sacs, eyes, ears, and nose of the subject.

17. The method of claim 10, wherein administering the composition comprises administering the composition without concurrent administration of a vaccine.

* * * * *

SEQUENCE LISTING

<160> NUMBER OF SEQ ID NOS: 2

<210> SEQ ID NO 1
<211> LENGTH: 2152
<212> TYPE: DNA
<213> ORGANISM: Artificial Sequence
<220> FEATURE:
<223> OTHER INFORMATION: Non-coding plasmid DNA and TLR3 agonist

<400> SEQUENCE: 1

```
taccctgaat tcatttcact tgcgactttg gctgcttttt gtatggtgaa ggatgcgccc      60
tggcgcgcat acacagcaca tctctttgca ggaaaaaaac gctgtgaaaa atgttggttt     120
tatcggctgg cgcggaatgg tcggctctgt tctcatgcaa cgcatggtag aggagcgcga     180
tttcgacgct attcgccctg ttttcttttc tacctcccag tttggacagg cggcgcccac     240
cttcggcgac acctccaccg gcacgctaca ggacgctttt gatctggatg cgctaaaagc     300
gctcgatatc atcgtgacct gccagggcgg cgattatacc aacgaaattt atccaaaagc     360
gcgcgaaagc ggatggcagg ttactggat tgatgcggct tctacgctgc gcatgaaaga      420
tgatgccatt attattctcg acccggtcaa ccaggacgtg attaccgacg gcctgaacaa     480
tggcgtgaag acctttgtgg gcggtaactg taccgttagc ctgatgttga tgtcgctggg     540
cggtctcttt gccataatc tcgttgactg ggtatccgtc gcgacctatc aggccgcctc      600
cggcggcggc gcgcgccata tgcgcagct gttaacccag atgggtcagt tgtatggcca      660
tgtcgccgat gaactggcga cgccgtcttc cgcaattctt gatattgaac gcaaagttac     720
ggcattgacc cgcagcggcg agctgccggt tgataacttt ggcgtaccgc tggcgggaag     780
cctgatcccc tggatcgaca aacagctcga taacggccag agccgcgaag agtggaaagg     840
ccaggcggaa accaacaaga ttctcaatac tgcctctgtg attccggttg atggtttgtg     900
tgtgcgcgtc ggcgcgctgc gctgtcacag ccaggcgttc accatcaagc tgaaaaaaga     960
ggtatccatt ccgacggtgg aagaactgct ggcggcacat aatccgtggg cgaaagtggt    1020
gccgaacgat cgtgatatca ctatgcgcga attaacccg gcggcggtga ccggcacgtt    1080
gactacgccg gttggtcgtc tgcgtaagct gaacatgggg ccagagttct tgtcggcgtt    1140
taccgtaggc gaccagttgt tatggggcgc cgccgagccg ctgcgtcgaa tgctgcgcca    1200
gttggcgtag tggctaataa aacgaaaggc tcagtcgaaa gactgggcct ttcgttttat    1260
gtcgactcgt cgttgtcgtt ttgtcgttag cttagctgcc aatcgttaag gtgcatcgat    1320 gcagggggc tgaattgcag tctatttgcg tcgtcgtttt gtcgttttgt cgttacgttc     1380
cggaagtcaa tcgattcgtc gttaacgtta acgctatgcc tccgatgcga atcagtctcg    1440
tcgttgtcgt tgtcgttcca tgctttacgt actactgctc gtcgctgttg tcgtttcttg    1500
tccaccctta agggccatct tcgtcgttgt cgttttgtcg ttctgattag tcccaatgct    1560
cgtggtgcat cgatgcaggg gggcgtaaac ctgctgaatc ggactcgtcg ttttgtcgtt    1620
ttgtcgttga tggccagctt taccatgact cgtcgttaac gttaacgcta tttactgatc    1680
ctgggatcca gtcgtcgttg tcgttgtcgt tatgccaagc tgccaatgtt tatcgtcgct    1740
gttgtcgttt cttgatatcc cggttgtcag ccgttaagtg ttcctgtgtc actcaaaatt    1800
gctttgagag gctctaaggg cttctcagtg cgttacatcc ctggcttgtt gtccacaacc    1860
gttaaacctt aaaagcttta aaagccttat atattctttt ttttcttata aaacttaaaa    1920
ccttagaggc tatttaagtt gctgatttat attaatttta ttgttcaaac atgagagctt    1980
agtacgtgaa acatgagagc ttagtacgtt agccatgaga gcttagtacg ttagccatga    2040
```

```
gggtttagtt cgttaaacat gagagcttag tacgttaaac ttgagagctt agtacgtgaa    2100
acatgagagc ttagtacgta ctatcaacag gttgaactgc gaattctcag at           2152

<210> SEQ ID NO 2
<211> LENGTH: 11
<212> TYPE: PRT
<213> ORGANISM: Artificial Sequence
<220> FEATURE:
<223> OTHER INFORMATION: a polycationic polymer polypeptide

<400> SEQUENCE: 2

Lys Leu Lys Leu Leu Leu Leu Leu Lys Leu Lys
1               5                   10
```